US011850227B2

(12) United States Patent
Zomorodi

(10) Patent No.: US 11,850,227 B2
(45) Date of Patent: *Dec. 26, 2023

(54) METHODS OF PROVIDING SOLRIAMFETOL THERAPY TO SUBJECTS WITH IMPAIRED RENAL FUNCTION

(71) Applicant: Axsome Malta Ltd., Qormi (MT)

(72) Inventor: Katayoun Zomorodi, San Jose, CA (US)

(73) Assignee: Axsome Malta Ltd., Qormi (MT)

( * ) Notice: Subject to any disclaimer, the term of this patent is extended or adjusted under 35 U.S.C. 154(b) by 0 days.

This patent is subject to a terminal disclaimer.

(21) Appl. No.: 18/194,503

(22) Filed: Mar. 31, 2023

(65) Prior Publication Data

US 2023/0248686 A1 Aug. 10, 2023

Related U.S. Application Data

(63) Continuation of application No. 17/479,121, filed on Sep. 20, 2021, which is a continuation of application No. 17/149,406, filed on Jan. 14, 2021, now Pat. No. 11,160,779, which is a continuation of application No. 16/824,560, filed on Mar. 19, 2020, now Pat. No. 10,940,133.

(51) Int. Cl.
*A61K 31/325* (2006.01)
*A61P 25/26* (2006.01)
*A61K 9/00* (2006.01)

(52) U.S. Cl.
CPC .......... *A61K 31/325* (2013.01); *A61K 9/0053* (2013.01); *A61P 25/26* (2018.01)

(58) Field of Classification Search
None
See application file for complete search history.

(56) References Cited

U.S. PATENT DOCUMENTS

| | | | |
|---|---|---|---|
| 4,335,138 A | 6/1982 | Wiersdorff et al. | |
| 5,705,640 A | 1/1998 | Choi et al. | |
| 5,756,817 A | 5/1998 | Choi et al. | |
| 5,955,499 A | 9/1999 | Choi et al. | |
| 6,140,532 A | 10/2000 | Choi et al. | |
| 6,562,867 B2 | 5/2003 | Plata-Salaman et al. | |
| 6,589,985 B2 | 7/2003 | Plata-Salaman et al. | |
| 6,680,299 B2 | 1/2004 | Or et al. | |
| 6,680,322 B2 | 1/2004 | Castelhano et al. | |
| 6,680,324 B2 | 1/2004 | Castelhano et al. | |
| 7,078,436 B2 | 7/2006 | Plata-Salaman et al. | |
| 8,232,315 B2 | 7/2012 | Lee et al. | |
| 8,440,715 B2 | 5/2013 | Ahnaou et al. | |
| 8,552,060 B2 | 10/2013 | Palumbo et al. | |
| 8,623,913 B2 | 1/2014 | Melnick et al. | |
| 8,729,120 B2 | 5/2014 | Sporn | |
| 8,741,950 B2 | 6/2014 | Khayrallah et al. | |
| 8,778,398 B2 | 7/2014 | Rourke et al. | |
| 8,877,806 B2 | 11/2014 | Ahnaou et al. | |
| 8,895,609 B2 | 11/2014 | Lee et al. | |
| 8,927,602 B2 | 1/2015 | Lee et al. | |
| 8,952,062 B2 | 2/2015 | Cook et al. | |
| 9,050,302 B2 | 6/2015 | Eller | |
| 9,226,910 B2 | 1/2016 | Khayrallah et al. | |
| 9,359,290 B2 | 6/2016 | Khayrallah et al. | |
| 9,403,761 B2 | 8/2016 | Kang et al. | |
| 9,585,863 B2 | 3/2017 | Khayrallah et al. | |
| 9,604,917 B2 | 3/2017 | Ahnaou et al. | |
| 9,610,274 B2 | 4/2017 | Lee et al. | |
| 9,649,291 B2 | 5/2017 | Khayrallah et al. | |
| 10,259,780 B2 | 4/2019 | Khayrallah et al. | |
| 10,351,517 B2 | 7/2019 | Ahnaou et al. | |
| 10,912,754 B2 | 2/2021 | Carter et al. | |
| 10,940,133 B1 | 3/2021 | Zomorodi | |
| 10,959,976 B2 | 3/2021 | Carter et al. | |
| 11,072,579 B2 | 7/2021 | Khayrallah et al. | |
| 11,160,779 B2 | 11/2021 | Zomorodi | |
| 11,648,232 B2 | 5/2023 | Carter et al. | |
| 2005/0080268 A1 | 4/2005 | Choi et al. | |
| 2005/0203130 A1 | 9/2005 | Buntinx | |
| 2008/0039529 A1 | 2/2008 | Sporn | |
| 2008/0090902 A1 | 4/2008 | Pandey et al. | |

(Continued)

FOREIGN PATENT DOCUMENTS

| CN | 105431142 A | 3/2016 |
|---|---|---|
| CN | 102946869 B | 8/2016 |

(Continued)

OTHER PUBLICATIONS

Bogan et al. "Effect of oral JZP-110 (ADX-N05) treatment on wakefulness and sleepiness in adults with narcolepsy," Sleep Medicine 16 (2015) 1102-1108; (Year: 2015).*
Carter et al. "A randomized, double-blind, placebo controlled, crossover study to evaluate the human abuse liability of solriamfetol, a selective dopamine and norepinephrine reuptake inhibitor," Journal of Psychopharmacology 2018, vol. 32(12) 1351-1361, 2018; (Year: 2018).*
WellButrin XL Insert, 2009. (Year: 2009).*
"U.S. Appl. No. 17/929,396; office action dated Jun. 6, 2023".
"U.S. Appl. No. 17/929,396; office action dated Oct. 4, 2023".
"U.S. Appl. No. 18/194,491; office action dated Jun. 23, 2023".
"U.S. Appl. No. 18/194,496; office action dated Aug. 3, 2023".
"U.S. Appl. No. 18/194,498; office action dated Jun. 29, 2023".
"U.S. Appl. No. 18/295,097; office action dated Aug. 24, 2023".
"U.S. Appl. No. 18/295,114; office action dated Sep. 14, 2023".
"U.S. Appl. No. 18/295,138; office action dated Oct. 4, 2023".
"U.S. Appl. No. 18/316,841; office action dated Sep. 7, 2023".
"U.S. Appl. No. 18/338,746; office action dated Sep. 29, 2023".

(Continued)

*Primary Examiner* — Jeffrey S Lundgren
*Assistant Examiner* — Michael J Schmitt

(57) ABSTRACT

The invention relates to methods for decreasing adverse effects associated with solriamfetol ([R]-2-amino-3-phenyl-propylcarbamate) therapy in subjects with impaired renal function. In particular, the invention provides an optimized dose escalation scheme for subjects with moderate renal impairment which results in the subjects having increased tolerance to adverse effects associated with the administration of solriamfetol. The invention also provides adjusted dosing for safe therapeutic use of solriamfetol in subjects having severe renal impairment.

25 Claims, 9 Drawing Sheets

(56) References Cited

U.S. PATENT DOCUMENTS

| | | |
|---|---|---|
| 2009/0312416 A1 | 12/2009 | Ahnaou et al. |
| 2010/0331332 A1 | 12/2010 | Lee et al. |
| 2011/0111027 A1 | 5/2011 | Rourke et al. |
| 2012/0004300 A1 | 1/2012 | Lee et al. |
| 2012/0142769 A1 | 6/2012 | Khayrallah et al. |
| 2012/0245226 A1 | 9/2012 | Lee et al. |
| 2012/0252892 A1 | 10/2012 | Lee et al. |
| 2013/0137761 A1 | 5/2013 | Prehm et al. |
| 2014/0275244 A1 | 9/2014 | Khayrallah et al. |
| 2014/0350098 A1 | 11/2014 | Ahnaou et al. |
| 2015/0018414 A1 | 1/2015 | Khayrallah et al. |
| 2015/0246874 A1 | 9/2015 | Kang et al. |
| 2016/0081970 A1 | 3/2016 | Khayrallah et al. |
| 2018/0064652 A1* | 3/2018 | Allphin .................. A61P 25/18 |
| 2020/0281886 A1 | 9/2020 | Carter et al. |
| 2021/0205227 A1 | 7/2021 | Allphin et al. |
| 2021/0205257 A1 | 7/2021 | Carter et al. |
| 2022/0000831 A1 | 1/2022 | Zomorodi |
| 2023/0233507 A1 | 7/2023 | Zomorodi |
| 2023/0233508 A1 | 7/2023 | Zomorodi |
| 2023/0233509 A1 | 7/2023 | Zomorodi |
| 2023/0263764 A1 | 8/2023 | Zomorodi |
| 2023/0285351 A1 | 9/2023 | Zomorodi |
| 2023/0293475 A1 | 9/2023 | Zomorodi |
| 2023/0310362 A1 | 10/2023 | Zomorodi |

FOREIGN PATENT DOCUMENTS

| | | |
|---|---|---|
| CN | 105848650 A | 8/2016 |
| EP | 0633023 A2 | 1/1995 |
| JP | 9503231 | 3/1997 |
| JP | 2012507532 A | 3/2012 |
| JP | 2013525480 A | 6/2013 |
| JP | 2016512531 A | 4/2016 |
| WO | 9607637 A1 | 3/1996 |
| WO | 9624577 A1 | 8/1996 |
| WO | 96032375 | 10/1996 |
| WO | 9815526 A1 | 4/1998 |
| WO | 98017636 | 4/1998 |
| WO | 2004010970 A1 | 2/2004 |
| WO | 2006050037 A1 | 5/2006 |
| WO | 2006133393 A1 | 12/2006 |
| WO | 2007001841 A1 | 1/2007 |
| WO | 2007018496 A1 | 2/2007 |
| WO | 2008048801 A2 | 4/2008 |
| WO | 2010053691 A1 | 5/2010 |
| WO | 2010150995 A2 | 12/2010 |
| WO | 2011005473 A2 | 1/2011 |
| WO | 2011055944 A2 | 5/2011 |
| WO | 2011055965 A2 | 5/2011 |
| WO | 2011139271 A1 | 11/2011 |
| WO | 2012002687 A2 | 1/2012 |
| WO | 2012002688 A2 | 1/2012 |
| WO | 2014164969 A1 | 10/2014 |
| WO | 2015006685 A1 | 1/2015 |
| WO | 2015010014 A1 | 1/2015 |
| WO | 2015130121 A1 | 9/2015 |

OTHER PUBLICATIONS

"U.S. Appl. No. 18/338,752; office action dated Sep. 14, 2023".
"U.S. Appl. No. 18/340,003; office action dated Oct. 6, 2023".
"U.S. Appl. No. 18/340,006; office action dated Sep. 1, 2023".
"Center for Drug Evaluation and Research: Summary Review", U.S. Food and Drugs Administration (2019).
"Dissolution Testing of Immediate Release Solid Oral Dosage Forms", U.S. Food and Drugs Administration, Guidance for Industry (1997).
"Notice of Opposition corresponding to European Patent No. 3509581 dated Aug. 8, 2023".
"Office Action corresponding to Korean Application No. 10-2019-7038340 dated Jul. 3, 2023".
"Sunosi, Assessment report", European Medicines Agency (2019).
Aulton, Michael E, "Pharmaceutics—The Science of Dosage Form Design", Churchill Livingston, Edinburgh, 2nd edition, 2002, pp. 1-12, 122 and 404-410.
Crump, Lauren Hartsell, et al., "Drug updates and approvals 2019 in review", The Nurse Practitioner, 44(12), 2019, 21-32.
Hsieh, Ming-Ju, et al., "Treating baclofen overdose by hemodialysi", American Journal of Emergency Medicine, 30(8), 2011, 1654-e5.
Jaussent, Isabelle, et al., "Impact of sleep disturbances on kidney function decline in the elderly", Eur Respir J 47:860-868 (2016).
Punjabi, Naresh M, "The Epidemiology of Adult Obstructive Sleep Apnea", Proceedings of the American Thoracic Society 5(2):136-143 (2008).
Roth, Thomas, et al., "Armodafinil improves wakefulness and long-term episodic memory in nCPAP-adherent patients with excessive sleepiness associated with obstructive sleep apnea", Sleep Breath 12:53-62 (2008).
Sullivan, Shannon S, et al., "Emerging drugs for common conditions of sleepiness: obstructive sleep apnea and narcolepsy", Expert Opin. Emerg. 20(4):571-582 (Nov. 24, 2015).
Tsume, Yasuhiro, et al., "The Biopharmaceutics Classification System: Subclasses for in vivo predictive dissolution (IPD) methodology and IVIVC", Eur. J. Pharm. Sci. 57:152-163 (Jan. 28, 2014).
Walz, J C, et al., "Daytime sleepiness, sleep disturbance and functioning impairment in bipolar disorder", Acta Neuropsychiatrica pp. 101-104 (Feb. 21, 2013).
Wolf, Erin, et al., "Baclofen Toxicity in Kidney Disease", American Journal of Kidney Diseases, 71(2), 2018, 275-280.
Wozniak, Dariusz R, et al., "Unmet needs of patients with narcolepsy: perspectives on emerging treatment options", Nat. Sci. Sleep 7:51-61 (2015).
Goodman & Gilman's "The Pharmacological Basis of Therapeutics. Section III. Drugs Acting on the Central Nervous System", McGraw-Hill Tenth Edition (2001) pp. 269, 284-285, and 638.
"Examination Report corresponding to European Application No. 18810236.2 dated Jul. 6, 2022".
"Office Action corresponding to Chinese Application No. 2018800493452 dated May 30, 2022".
"Office Action corresponding to Japanese Application No. 2020-516785 dated Feb. 22, 2022".
"Written Opinion corresponding to Singapore Application No. 11201901996U dated May 16, 2022".
"Anonymous, ClinicalTrials.gov, NCT02348593, "Twelve-week Study of the Safety and Efficacy of JZP-110 in the Treatment of Excessive Sleepiness in Narcolepsy", Jul. 23, 2019".
"Anonymous, ClinicalTrials.gov, NCT02348606, "Twelve-week Study of the Safety and Efficacy of JZP-110 in the Treatment of Excessive Sleepiness in OSA" OSA, Jul. 23, 2019".
"Anonymous, ClinicalTrials.gov, NCT02806895 "Study Accessing Effects of JZP-110 on Driving Performance in the Treatment of Excessive Sleepiness in OSA" (Jun. 2016)".
"Anonymous, ClinicalTrials.gov, NCT02806908 "Study Accessing Effects of JPZ-110 on Driving Performance in the Treatment of Excessive Sleepiness in Narcolepsy" (Jun. 2016)".
"U.S. Appl. No. 16/225,890; office action dated May 17, 2019".
"U.S. Appl. No. 16/618,735; office action dated Jul. 29, 2020".
"U.S. Appl. No. 16/877,717; office action dated Jul. 28, 2020".
"U.S. Appl. No. 17/034,564; office action dated Jan. 12, 2022".
"U.S. Appl. No. 17/034,564; office action dated Jul. 28, 2022".
"U.S. Appl. No. 17/149,406; office action dated Mar. 8, 2021".
"Aulton, "Dissolution and solubility", Aug. 2, 2015, retrieved from https://clinicalgate.com/dissolution-and-solubility on May 13, 2018. (Year: 2015)".
"Diagnostic and Statistical Manual of Mental Disorders, Fourth Edition, Published by the American Psychiatric Association Washington, DC.", pp. 345-429 and 597-663 (Mar. 2010).
"Examination Report corresponding to Australian Application No. 2017324855 dated Apr. 28, 2021".
"Examination Report corresponding to Australian Application No. 2017324855 dated Feb. 17, 2021".
"Examination Report corresponding to Australian Application No. 2018278332 dated May 4, 2021".
"Examination Report corresponding to Chilean Application No. 571-2019 dated Jan. 20, 2021".

(56) References Cited

OTHER PUBLICATIONS

"Examination Report corresponding to European Application No. 17849426.6 dated Jun. 7, 2021".
"Examination Report corresponding to European Application No. 17849426.6 dated Mar. 16, 2021".
"Examination Report corresponding to European Application No. 18810236.2 dated Nov. 15, 2021".
"Extended European Search Report corresponding to European Application No. 17849426.6 dated Mar. 5, 2020".
"Fava, M. (2004) The Journal of Psychiatry, 65 (suppl16, 27-32)-abstract".
"International Preliminary Report on Patentability corresponding to International Application No. PCT/US2018/035532 dated Dec. 12, 2019".
"International Search Report and Written Opinion corresponding to International Application No. PCT/US2006/022407 dated Nov. 13, 2006".
"International Search Report and Written Opinion Corresponding to International Application No. PCT/US2006/022407; dated Nov. 13, 2006; 3 Pages".
"International Search Report and Written Opinion corresponding to International Application No. PCT/US2018/035532 dated Aug. 30, 2018".
"International Search Report corresponding to Singapore Application No. 11201901996U dated May 2, 2020".
"Merck Manual, 1999, Symptoms and Signs, Treatment, p. 1415".
"Narcolepsy: Treatment Issues, Thomas Roth (J Clin Psychiatry 2007;68 [suppl 13]:16-19)".
"Notification of Transmittal of International Preliminary Report on Patentability and Written Opinion corresponding to PCT/US2017/050221, dated Mar. 21, 2019".
"Notification of Transmittal of the International Search Report and the Written Opinion of the International Searching Authority, or the Declaration corresponding to International Application No. PCT/US2017/050221 dated Nov. 13, 2017".
"Office Action corresponding to Japanese Application No. 2019-512901 dated Sep. 28, 2021".
"Office Action corresponding to Brazilian Application No. 112019025286-0 dated Jun. 3, 2022".
"Office Action corresponding to Brazilian Application No. BR112019004479-5 dated Jul. 5, 2021".
"Office Action corresponding to Chilean Patent Application No. 571-2019 dated Dec. 1, 2021".
"Office Action corresponding to Chinese Application No. 201780068148.0 dated Jun. 11, 2021".
"Office Action corresponding to Chinese Application No. 2017800681480 dated Mar. 2, 2022".
"Office Action corresponding to Chinese Application No. 2018800493452 dated Dec. 12, 2022".
"Office Action corresponding to Chinese Application No. 2018800493452 dated Feb. 21, 2022".
"Office Action corresponding to Chinese Application No. 2018800493452 dated Jul. 28, 2021".
"Office Action corresponding to Indian Application No. 201917013067 dated Dec. 23, 2020".
"Office Action corresponding to Indonesian Application No. PID201902735 dated Jul. 27, 2021".
"Office Action corresponding to Indonesian Application No. PID201902735 dated Oct. 29, 2021".
"Office Action corresponding to Indonesian Application No. PID201902735 dated Mar. 18, 2021".
"Office Action corresponding to Japanese Application No. 2019-512901 dated Apr. 23, 2021".
"Office Action corresponding to Japanese Application No. 2019-512901 dated Jun. 10, 2022".
"Office Action corresponding to Japanese Application No. 2020-516785 dated Jan. 17, 2023".
"Office Action corresponding to Japanese Application No. 2020-516785 dated Jul. 5, 2022".
"Office Action corresponding to Korean Application No. 10-2019-7009893 dated Feb. 25, 2022".
"Office Action corresponding to Korean Application No. 10-2019-7038348 dated Mar. 6, 2023".
"Office Action corresponding to Malaysian Application No. PI2019001181 dated Dec. 27, 2022".
"Office Action corresponding to Mexican Application No. MX/A/2019/002606 dated Jun. 8, 2021".
"Office Action corresponding to Mexican Application No. MX/A/2019/014409 dated May 19, 2021".
"Office Action corresponding to Mexican Application No. MX/A/2019/014409 dated Aug. 10, 2021".
"Office Action corresponding to Mexican Application No. MX/A/2019/014409 dated Oct. 15, 2021".
"Office Action corresponding to Philippine Application No. 1-2019-500494 dated Nov. 25, 2022".
"Office Action corresponding to Philippine Application No. 1-2019-500494 dated Dec. 17, 2021".
"Office Action corresponding to Russian Application No. 2019110127 dated Jul. 2, 2021".
"Office Action corresponding to Singapore Application No. 11201911470V dated Sep. 5, 2022".
"Office Action corresponding to South African Application No. 519401246 dated Jul. 28, 2021".
"Phenprobamate, Wikipedia, https://en.wikipedia.org/wiki/Phenprobamate, last edited Apr. 2, 2016, accessed Sep. 24, 2019".
"Rejection Decision corresponding to Brazilian Application No. PI0613697-4 dated Jan. 25, 2011".
"Sunosi package insert Mar. 20, 2019".
"SUPAC-IR: Immediate-Release Solid Oral Dosage Forms: Scale-Up and Post-Approval Changes: Chemistry, Manufacturing and Controls, In Vitro Dissolution Testing, and In Vivo Bioequivalence Documentation; Issued by: U.S. Department of Health and Human Services,".
"The Search Report by the Taiwan Intellectual Property Office, dated Dec. 14, 2011. In the corresponding Taiwanese patent application No. 95120134. (English translation only.)".
"U.S. FDA Guidance for Industry, Pharmacokinetics in Patients with Impaired Renal Function—Study Design, Data Analysis, and Impact on Dosing and Labeling", Mar. 2010 Clinical Pharmacology Revision 1. (Year: 2010).
"Written Opinion corresponding to Brazil Application No. PI0920543-8 dated Dec. 18, 2018".
"Written Opinion corresponding to Singapore Application No. 11201901996U dated Jun. 29, 2021".
"Written Opinion corresponding to Singapore Application No. 11201901996U dated May 6, 2020".
Amsterdam, et al., "A single-site, double-blind, placebo-controlled, dose-ranging study of YKP10A-a putative, new antidepressant", Progress in Neuro-Psychopharmacology & Biological Psychiatry 26:1333-1338 (2002).
Arnulf, et al., "(Neurology; Apr. 9, 2002, vol. 58, No. 7, 1 019-1 024 )-abstract".
Black JE, , et al., ""Narcolepsy and syndromes of primary excessive daytime somnolence" seminars in Neurology 2004; 24(3):271-262".
Bogan, et al., ""Effect of oral JZP-110 (ADX-N05) treatment on wakefulness and sleepiness in adults with narcolepsy", Sleep Medicine 16(9):1102-1108 (2015)".
Fox, Laura Moore, "The Science and Practice of Pharmacy, 21st Edition", American Journal of Pharmaceutical Education 70(3) Article 71 (2006).
Gordon, Robert, Receptor Binding and Uptake Studies of YKP10A Using NovaScreen Report No. NovaScreen 870 & 871, Pharmacology Group P-Project Yukong Limited vol. 3:130-155 (Oct. 24, 1994).
Gordon, et al., "Abstracts of the 28th Annual Meeting, Soc. NeuroSci. 24:1490 (1998)".
Hasan, et al., "Neuropsychopharmacology 34:1625 (2009)".
Johns, Murray W, "A New Method for Measuring Daytime Sleepiness: The Epworth Sleepiness Scale", Sleep 14(6):540-545 (Dec. 1991).
Lammers, et al., "Pharmacological management of narcolepsy", Expert Opin. Pharmacother. 2003 vol. 4 No. 10 pp. 1739-1746.

(56) References Cited

OTHER PUBLICATIONS

Li, Shoufeng, et al., "Investigation of Solubility and Dissolution of a Free Base and Two Different Salt Forms as a Function of pH", Pharmaceutical Research 22(4):628-635 (Apr. 7, 2005).
Pertsev, I. M., "Pharmaceutical and biomedical aspects of drugs: 2 volumes", vol. 1.—Kharkov: UkrFA. 1999.—464 pages, pp. 252-254.
Poryazova, et al., ""Excessive Daytime Sleepiness in Parkinson's Disease: Characteristics and Determinants", Eur. Neurol. 63:129-135 (2010)".
Riemann, Dieter, et al., "Sleep and Depression—results from psychobiological studies: an overview", Biological Psychology 57:67-103 (2001).
Ruoff, et al., "Effect of Oral JZP-110 (ADX-N05) on Wakefulness and Sleepiness in Adults with Narcolepsy: A Phase 2b Study", Sleep 39(7):1379-1387 (2016).
Ruoff, et al., "Evaluation of the effect of JZP-110 in patients with narcolepsy assessed using the Maintenance of Wakefulness Test censored to 20 minutes", J. Sleep Med. 35:12-16 (2017).
Schweitzer, et al., ""A Phase 3, Randomized, Placebo-Controlled, Double-Blind, 12-Week, Multicenter Study of the Efficacy and Safety of JZP-110 for the Treatment of Excessive Sleepiness in Patients with Obstructive Sleep Apnea", Sleep 40:A237 (Abstract Supplement)".
Schweitzer, Paula K., et al., "Solriamfetol for Excessive Sleepiness in Obstructive Sleep Apnea (Tones 3) a Randomized Controlled Trial", American Journal of Respiratory and Critical Care Medicine 199(11):1421-1431 (Jun. 1, 2019).
Scrima, et al., "Identifying clinically important difference on the Epworth Sleepiness Scale: results from a narcolepsy clinical trial of JZP-110", J. Sleep Med. 38:108-112 (2017).
Strollo, P. J., et al., "A phase 3, Placebo-Controlled, Randomized Withdrawal, Double-Blind, 6-Week Multicenter Study of the Safety and Efficacy of JZP-110 for the Treatment of Excessive Sleepiness in Participants with Obstructed Sleep Apena", Sleep vol. 40:A238, Abstract Supplement, (2017) 1 page.
Thorpy, M. J., et al., "A Randomized, Placebo-Controlled, Phase 3 Study of the Safety and Efficacy of Solriamfetol (JZP-110) for the Treatment of Excessive Sleepiness in Patients with Narcolepsy", Sleep Medicine 40:e186-e363, Abstracts, (2017) p. e327.
Uzunovic, et al., ""Effect of Magnesium Stearate Concentration on Dissolution Properties of Ranitidine Hydrochloride Coated Tablets", Bosnian Journal of Basic Medical Sciences 7(3):279-283 (2007)".
Zomorodi, et al., ""An Open-Label, Single-Dose, Phase 1 Study of the Pharmacokinetics and Safety of JZP-110 in Subjects With Normal or Impaired Renal Function and With End-Stage Renal Disease Requiring Hemodialysis," Sleep, vol. 40, Abstract Supplement, 2017 A382; (Year:".
Zomorodi, K., et al., "An Open-Label, Single-Dose, Phase 1 Study of the Pharmacokinetics and Safety of JZP-110 in Subjects with Normal or Impaired Renal Function and with End-Stage Renal Disease Requiring Hemodialysis", Sleep vol. 40, Abstract Supplement, A382 (2017) 1 page.
Zomorodi, et al., "Poster 291, An Open-Label, Single-Dose, Phase 1 Study of the Pharmacokinetics and Safety of JZP-110 in Subjects with Normal or Impaired Renal Function and with End-Stage Renal Disease Requiring Hemodialysis", Sleep 2017, the 31st Annual Meeting of the Associate Professional Sleep Societies, Jun. 3-7, 2017.
Zomorodi, Katie, et al., "Poster 291, Sleep 2017, the 31st Annual Meeting of the Associate Professional Sleep Societies, Jun. 3-7, 2017".
Zomorodi, et al., "Poster T-038, Population Pharmacokinetic Analysis of Solriamfetol (JPZ-110), a Selective Dopamine and Norepinephrine Uptake Inhibitor", The Ninth American Conference on Pharmacometrics (ACoP9), Oct. 7-10, 2018.
Zomorodi, Katie, et al., "Poster T-038, The Ninth American Conference on Pharmacometrics (ACoP9), Oct. 7-10, 2018".
Zomorodi, Katie, et al., "Single-Dose Pharmacokinetics and Safety of Solriamfetol in Participants With Normal or Impaired Renal Function and With End-Stage Renal Disease Requiring Hemodialysis", The Journal of Clinical Pharmacology 59(8):1120-1129 (2019).

\* cited by examiner

METHODS OF PROVIDING SOLRIAMFETOL THERAPY TO SUBJECTS WITH IMPAIRED RENAL FUNCTION

STATEMENT OF PRIORITY

This application is a continuation of and claims priority to U.S. patent application Ser. No. 17/479,121, filed Sep. 20, 2021, which is a continuation of and claims priority to U.S. patent application Ser. No. 17/149,406, filed Jan. 14, 2021, now U.S. Pat. No. 11,160,779, which is a continuation of and claims priority to U.S. patent application Ser. No. 16/824,560, filed Mar. 19, 2020, now U.S. Pat. No. 10,940,133, the entire contents of each of which is incorporated by reference herein in its entirety.

FIELD OF THE INVENTION

The invention relates to methods for decreasing adverse effects associated with solriamfetol ([R]-2-amino-3-phenyl-propylcarbamate) therapy in subjects with impaired renal function. In particular, the invention provides an optimized dose escalation scheme for subjects with moderate renal impairment which results in the subjects having increased tolerance to adverse effects associated with the administration of solriamfetol. The invention also provides adjusted dosing for safe therapeutic use of solriamfetol in subjects having severe renal impairment.

BACKGROUND OF THE INVENTION

APC and its phenylalanine analogs have demonstrated application in the treatment of a variety of disorders, including excessive daytime sleepiness, cataplexy, narcolepsy, fatigue, depression, bipolar disorder, fibromyalgia, attention deficit/hyperactivity disorder and others. See, for example, U.S. Pat. Nos. 8,232,315; 8,440,715; 8,552,060; 8,623,913; 8,729,120; 8,741,950; 8,895,609; 8,927,602; 9,226,910; 9,359,290; and 9,610,274 and U.S. Publication No. 2015/0018414. The structure of the free base of APC is given below as Formula I.

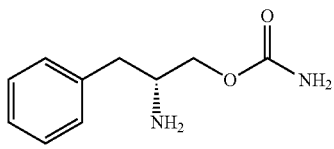

(I)

Those of skill in the art will appreciate that methods for producing APC (which also has other names) and related compounds can be found in U.S. Pat. Nos. 5,955,499; 5,705,640; 6,140,532 and 5,756,817.

[R]-2-amino-3-phenylpropylcarbamate hydrochloride (APC-HCl) is a selective dopamine and norepinephrine reuptake inhibitor. At micromolar concentrations, APC-HCl can selectively bind and inhibit reuptake at dopamine and norepinephrine transporters without promoting monoamine release (See, Carter L, Baladi M, Black J, JZP-110: a dopamine-norepinephrine reuptake inhibitor (DNRI) with robust wake-promoting effects and low abuse potential. Poster presented at: Winter Conference on Brain Research; Jan. 23-28, 2016; Breckenridge, Colorado. Poster #Su23, 2016; and Baladi M G, Forster M J, Gatch M B, et al., Characterization of the neurochemical and behavioral effects of solriamfetol (JZP-110), a selective dopamine and norepinephrine reuptake inhibitor. *J Pharmacol Exp Ther.* 2018; 366:367-376).

As those of skill may recognize, APC-HCl (also referred to as solriamfetol HCl) has been approved by the FDA and EMA as a wake-promoting agent for the treatment of excessive daytime sleepiness associated with narcolepsy and obstructive sleep apnea (OSA). Phase 3 trials conducted with APC-HCl on patients having narcolepsy and OSA demonstrated statistically significant reductions in excessive daytime sleepiness measured on the patient-reported Epworth Sleepiness Scale and improvement in objective assessment of wakefulness using the Maintenance of Wakefulness Test. Significantly higher percentages of participants treated with APC-HCl in these trials also reported improvement on the Patient Global Improvement of Change scale relative to placebo at all evaluated time points. See, Johns M W, A new method for measuring daytime sleepiness: the Epworth Sleepiness Scale. *Sleep.* 1991; 14(6):540-545); Thorpy M J, Dauvilliers Y, Shapiro C, et al., A randomized, placebo-controlled, phase 3 study of the safety and efficacy of JZP-110 for the treatment of excessive sleepiness in patients with narcolepsy, *Sleep,* 2017; 40 (suppl): A250; Schweitzer P K, Rosenberg R, Zammit G K, et al., Solriamfetol for excessive sleepiness in obstructive sleep apnea (TONES 3): a randomized controlled trial, *Am J Respir Crit Care Med.* 2018; Dec. 6; and Strollo P J, Jr., Hedner J, Collop N, et al., Solriamfetol for the treatment of excessive sleepiness in obstructive sleep apnea: A placebo-controlled randomized-withdrawal study. *Chest.* 2018; Nov. 21.

The most common adverse reactions or effects associated with APC-HCl therapy include headache, nausea, decreased appetite, anxiety, nervousness, panic attack, dry mouth, and diarrhea. Many of these effects can interfere with everyday activities and quality of life. Data from 12-week placebo-controlled clinical trials comparing various doses of solriamfetol support the conclusion that these adverse effects are dose-dependent and that they are exacerbated when APC-HCl is administered at higher doses. Additionally, solriamfetol has been shown to rely on renal excretion of unchanged drug as its primary route of elimination. The fact that the mean renal clearance of APC-HCl is 3 times the glomerular filtration rate suggest that its renal clearance is most likely attributed to a combination of passive diffusion and active renal tubular secretion by multiple cation transporters working in concert, with minimal tubular reabsorption. Therefore, administration of APC-HCl to patients with impaired renal function (which entails reduced passive diffusion and active renal tubular secretion) would be expected to result in higher APC-HCl exposure in this patient population. Prior to the present inventor's discovery however, it was not known what dose, if any, or escalation of APC-HCl would be safe for the renally impaired given the drug's unique pharmacological profile.

SUMMARY OF THE INVENTION

The present invention addresses an unmet medical need by providing methods of administering APC-HCl to renally impaired subjects in a manner that minimizes adverse effects. Of the methods provided is a dose escalation scheme for administering APC-HCl to patients with mild renal impairment, which involves an initial daily dose equivalent to 75 mg APC and waiting until after at least 3 days to reach the maximum daily dose equivalent to 150 mg APC. In another aspect of the invention, the dose escalation scheme of the present invention provides APC-HCl to patients with moderate renal impairment at an initial daily dose equivalent to 37.5 mg APC and in a manner such that maximum dosage is not reached until after at least five days (in some embodiments of the invention, at least seven days); the method allows for a maximum dosage equivalent to 75 mg APC per day to be administered to a patient so as to reduce the incidence of adverse effects associated with the administration of APC-HCl by tailoring dose escalation to account for tolerance development in the patient. For patients with severe renal impairment (who have further reduced passive diffusion and active renal tubular secretion as compared with moderately impaired patients), the invention provides an alternative dosing regimen involving a daily maximum dose equivalent to 37.5 mg APC. The present inventor, based on analyses of the pharmacokinetics and safety profile of APC-HCl in conjunction with population PK simulations, has additionally discovered that use of APC-HCl should be avoided for patients with end-stage renal disease (with or without hemodialysis).

As such, provided according to embodiments of the present invention are methods of providing APC-HCl to a renally impaired subject in need thereof according to a dose escalation regimen, the method comprising providing to the subject a first oral daily dose equivalent to 37.5 mg APC from day one to day $n_1$ of the dose escalation regimen; and providing to the subject a second oral daily dose equivalent to 75 mg APC starting on day $n_2$ of the dose escalation regimen, wherein $n_1$ is an integer equal to or greater than 5 and $n_2$ is equal to the sum of $n_1+1$, wherein the renally impaired subject is not provided a daily dose exceeding a dose equivalent to 75 mg APC, and wherein the renally impaired subject has an estimated glomerular filtration rate (eGFR) of about 30 mL/min/1.73 $m^2$ to about 59 mL/min/1.73 $m^2$.

Further provided according to embodiments of the invention are methods of providing APC-HCl to a renally impaired subject with narcolepsy in need thereof, the method comprising providing to the subject an oral daily dose equivalent to 37.5 mg APC, wherein the renally impaired subject is not provided a daily dose exceeding a dose equivalent 37.5 mg APC; and wherein the renally impaired subject has an eGFR of about 15 ml/min/1.73 $m^2$ to about 29 ml/min/1.73 $m^2$.

Further provided according to embodiments of the invention are methods of treating excessive daytime sleepiness in a renally impaired subject with narcolepsy in need thereof, comprising administering to the subject APC-HCl at an initial dose equivalent to 37.5 mg APC once daily; wherein the subject has an estimated glomerular filtration rate of 30-59 ml/min/1.73 $m^2$; thereby treating excessive daytime sleepiness in the subject.

Further provided according to embodiments of the invention are methods of treating excessive daytime sleepiness in a renally impaired subject with narcolepsy in need thereof, comprising administering to the subject APC-HCl at a maximum dose equivalent to 37.5 mg APC once daily; wherein the subject has an estimated glomerular filtration rate of 15-29 ml/min/1.73 $m^2$; thereby treating excessive daytime sleepiness in the subject.

Further provided according to embodiments of the invention are methods of guiding APC therapy in a renally impaired subject with narcolepsy in need thereof, comprising: (a) determining if the subject has mild renal impairment (an estimated glomerular filtration rate of 60-89 ml/min/1.73 $m^2$), moderate renal impairment (an estimated glomerular filtration rate of 30-59 ml/min/1.73 $m^2$), severe renal impairment (an estimated glomerular filtration rate of 15-29 ml/min/1.73 $m^2$), or end stage renal disease (an estimated glomerular filtration rate of less than 15 ml/min/1.73 $m^2$); and (b) administering to the subject APC-HCl according to a regimen recommended for subjects without renal impairment if the subject has mild renal impairment, said regimen comprising an initial dose equivalent to 75 mg APC once daily and a maximum dose equivalent to 150 mg APC once daily; or administering to the subject APC-HCl at an initial dose equivalent to 37.5 mg APC once daily and a maximum dose equivalent to 75 mg APC once daily if the subject has moderate renal impairment; or administering to the subject APC-HCl at a maximum dose equivalent to 37.5 mg APC once daily if the subject has severe renal impairment; or not administering to the subject APC-HCl if the subject has end stage renal disease.

Further provided according to embodiments of the invention are methods of guiding APC therapy in a renally impaired subject with obstructive sleep apnea in need thereof, comprising: (a) determining if the subject has mild renal impairment (an estimated glomerular filtration rate of 60-89 ml/min/1.73 $m^2$), moderate renal impairment (an estimated glomerular filtration rate of 30-59 ml/min/1.73 $m^2$), severe renal impairment (an estimated glomerular filtration rate of 15-29 ml/min/1.73 $m^2$), or end stage renal disease (an estimated glomerular filtration rate of less than 15 ml/min/1.73 $m^2$); and (b) administering to the subject APC-HCl according to a regimen recommended for subjects without renal impairment if the subject has mild renal impairment, said regimen comprising an initial dose equivalent to 37.5 mg APC once daily and a maximum dose equivalent to 150 mg APC once daily; or administering to the subject APC-HCl at an initial dose equivalent to 37.5 mg APC once daily and a maximum dose equivalent to 75 mg APC once daily if the subject has moderate renal impairment; or administering to the subject APC-HCl at a maximum dose equivalent to 37.5 mg APC once daily if the subject has severe renal impairment; or not administering to the subject APC-HCl if the subject has end stage renal disease.

Further provided according to embodiments of the invention are methods of treating excessive daytime sleepiness in a renally impaired subject with obstructive sleep apnea in need thereof, comprising administering to the subject APC-HCl at an initial dose equivalent to 37.5 mg APC once daily, wherein the subject has an estimated glomerular filtration rate of 30-59 ml/min/1.73 $m^2$, thereby treating excessive daytime sleepiness in the subject.

Further provided according to embodiments of the invention are methods of treating excessive daytime sleepiness in a renally impaired subject with obstructive sleep apnea in need thereof, comprising administering to the subject APC-HCl at a maximum dose equivalent to 37.5 mg APC once daily; wherein the subject has an estimated glomerular filtration rate of 15-29 ml/min/1.73 $m^2$, thereby treating excessive daytime sleepiness in the subject.

Further provided according to embodiments of the invention are methods of reducing toxicity of APC-HCl therapy in a renally impaired subject, comprising: administering to the subject APC-HCl at an initial dose equivalent to 37.5 mg APC once daily; increasing the daily dose to a maximum dose equivalent to 75 mg APC after at least 7 days; wherein the subject has an estimated glomerular filtration rate of 30-59 ml/min/1.73 $m^2$, thereby reducing toxicity of APC-HCl therapy in the subject.

Further provided according to embodiments of the invention are methods of reducing toxicity of APC-HCl therapy in a renally impaired subject, comprising administering to the subject APC-HCl at a maximum dose equivalent to 37.5 mg APC once daily; wherein the subject has an estimated glomerular filtration rate of 15-29 ml/min/1.73 m², thereby reducing toxicity of APC-HCl in the subject.

Further provided according to embodiments of the invention are methods of reducing toxicity of APC-HCl therapy in a renally impaired subject, comprising: (a) determining if the subject has mild renal impairment (an estimated glomerular filtration rate of 60-89 ml/min/1.73 m²), moderate renal impairment (an estimated glomerular filtration rate of 30-59 ml/min/1.73 m²), severe renal impairment (an estimated glomerular filtration rate of 15-29 ml/min/1.73 m²), or end stage renal disease (an estimated glomerular filtration rate of <15 ml/min/1.73 m²); and (b) administering to the subject APC-HCl at a dose of APC-HCl recommended for subjects without renal impairment if the subject has mild renal impairment, wherein the dose of APC-HCl recommended for subjects without renal impairment comprises an initial dose equivalent to 75 mg APC once daily and a maximum dose equivalent to 150 mg APC once daily after at least 3 days; or administering to the subject APC-HCl at an initial dose equivalent to 37.5 mg APC once daily and a maximum dose equivalent to 75 mg APC once daily after at least 7 days if the subject has moderate renal impairment; or administering to the subject APC-HCl at a maximum dose equivalent to 37.5 mg APC once daily if the subject has severe renal impairment; or not administering to the subject APC-HCl if the subject has end stage renal disease. In some embodiments of the invention, the subject is being treated with the above dosing regimen for excessive daytime sleepiness associated with narcolepsy.

In other embodiments of the invention, methods of reducing toxicity of APC-HCl therapy in a renally impaired subject with obstructive sleep apnea comprise: (a) determining if the subject has mild renal impairment (an estimated glomerular filtration rate of 60-89 ml/min/1.73 m²), moderate renal impairment (an estimated glomerular filtration rate of 30-59 ml/min/1.73 m²), severe renal impairment (an estimated glomerular filtration rate of 15-29 ml/min/1.73 m²), or end stage renal disease (an estimated glomerular filtration rate of <15 ml/min/1.73 m²); and (b) administering to the subject APC-HCl at a dose of APC-HCl recommended for subjects without renal impairment if the subject has mild renal impairment, wherein the dose of APC-HCl recommended for subjects without renal impairment comprises an initial dose equivalent to 37.5 mg APC once daily and doubling the dose at intervals of at least 3 days to a maximum dose equivalent to 150 mg APC; or administering to the subject APC-HCl at an initial dose equivalent to 37.5 mg APC once daily and a maximum dose equivalent to 75 mg APC once daily after at least 7 days if the subject has moderate renal impairment; or administering to the subject APC-HCl at a maximum dose equivalent to 37.5 mg APC once daily if the subject has severe renal impairment; or not administering to the subject APC-HCl if the subject has end stage renal disease.

The present invention is explained in greater detail in the drawings herein and the specification set forth below.

DETAILED DESCRIPTION OF THE INVENTION

Figure 1A:
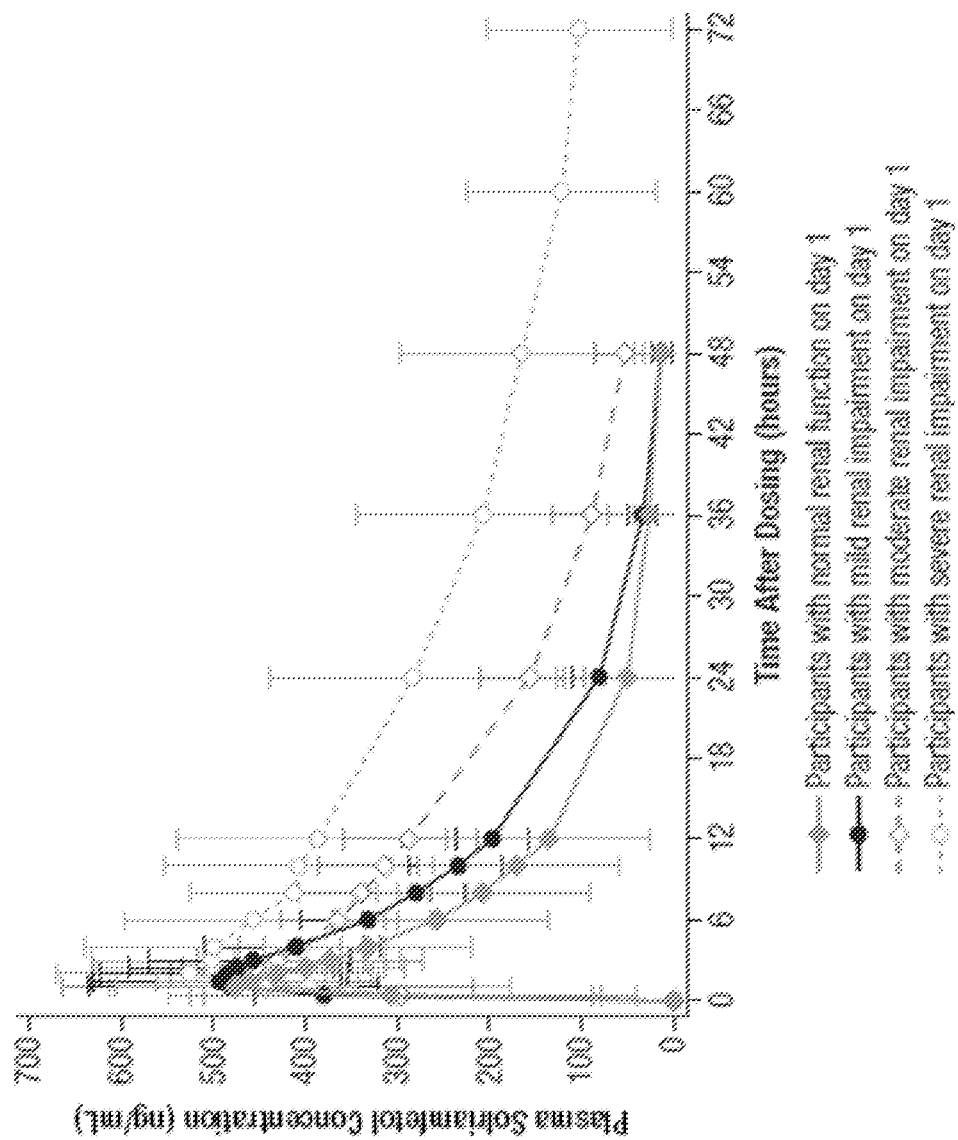
FIG. 1A shows the mean (SD) plasma of APC-HCl concentration-time profiles following a single dose equivalent to 75-mg APC for participants with normal renal function and mild-to-severe renal impairment.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

All publications, patent applications, patents, and other references mentioned herein are incorporated by reference herein in their entirety for all purposes.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

The term "therapeutically effective amount" or "effective amount," as used herein, refers to that amount of a composition, compound, or agent of this invention that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, etc., as would be well known in the art.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science;* 21$^{st}$ ed. 2005).

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The compound [R]-2-amino-3-phenylpropylcarbamate (APC) or solriamfetol is also named (R)-(beta-amino-benzenepropyl) carbamate or O-carbamoyl-(D)-phenylalaninol and has alternatively been called ADX-N05, SKL-N05, SK-N05, YKP10A, and R228060. The hydrochloride salt of the compound is named [R]-2-amino-3-phenylpropylcarbamate hydrochloride (APC-HCl) or solriamfetol HCl.

A "disorder or condition amenable to treatment" refers to any disorder or condition in which administration of APC to a subject results in the treatment of one or more symptoms of the disorder in the subject. Disorders amenable to treatment with APC include, without limitation, excessive daytime sleepiness, fatigue, drug addiction, sexual dysfunction, depression, fibromyalgia syndrome, attention deficit/hyperactivity disorder, restless legs syndrome, bipolar disorder, cataplexy, obesity, and smoking cessation.

In some embodiments, APC may be used to treat and/or prevent excessive daytime sleepiness (EDS). See U.S. Pat. Nos. 8,440,715; 8,877,806; 9,604,917; and 10,351,517; incorporated by reference herein in their entirety. EDS may be due to, without limitation, a central nervous system (CNS) pathologic abnormality, stroke, narcolepsy, idiopathic CNS hypersomnia, sleep deficiency, sleep apnea, obstructive sleep apnea, insufficient nocturnal sleep, chronic pain, acute pain, Parkinson's disease, urinary incontinence, multiple sclerosis fatigue, attention deficit hyperactivity disorder, Alzheimer's disorder, bipolar disorder, cardiac ischemia, misalignments of the body's circadian pacemaker with the environment, or jet lag; or a subject doing shift work or taking sedating drugs.

In some embodiments, APC may be used to treat and/or prevent fatigue. See U.S. Pat. Nos. 8,741,950; 9,464,041; 9,999,609; and 10,507,192; incorporated by reference herein in their entirety. Fatigue may be due to, without limitation, a disease, disorder or condition such as depression, cancer, multiple sclerosis, Parkinson's disease, Alzheimer's disease, chronic fatigue syndrome, fibromyalgia, chronic pain, traumatic brain injury, AIDS, and osteoarthritis. Fatigue may be due to, without limitation, a treatment or medication such as chemotherapy, radiation therapy, bone marrow transplant, and anti-depressant treatment.

In some embodiments, APC may be used to treat drug addiction. See U.S. Pat. No. 8,232,315, incorporated by reference in its entirety. In some embodiments, the addicted drug may be nicotine, opioid, cocaine, amphetamine, methamphetamine, ethanol, heroin, morphine, phencyclidine (PCP), and methylenedioxymethamphetamine (MDMA).

In some embodiments, APC may be used to treat sexual dysfunction. See U.S. Pat. No. 8,552,060, incorporated by reference herein in its entirety. In some embodiments, the treatment may increase interest in sex and/or the ability to have an orgasm. In some embodiments, the sexual dysfunction may be due to treatment with a therapeutic agent, including without limitation, selective serotonin reuptake inhibitors (SSRIs); selective serotonin and norepinephrine reuptake inhibitors (SNRIs); older tricyclic antidepressants (TCAs); monoamine oxidase inhibitors (MAO-inhibitors), reversible inhibitors of monoamine oxidase (RIMAs), tertiary amine tricyclics and secondary amine tricyclic antidepressants, e.g., therapeutic agents such as fluoxetine, duloxetine, venlafaxine, milnacipran, citalopram, fluvoxamine, paroxetine, sertraline, 5-MCA-NAT, lithium carbonate, isocarboxazid, phenelzine, tranylcypromine, selegiline, moclobemide, kappa opioid receptor antagonists; selective neurokinin antagonists, corticotropin releasing factor (CRF) antagonists, antagonists of tachykinins, α-adrenoreceptor antagonists, amitriptyline, clomipramine, doxepin, imipramine, venlafaxine, trimipramine, amoxapine, desipramine, maprotiline, nortriptyline and protriptyline, and pharmaceutically acceptable salts thereof.

In some embodiments, APC may be used as an adjunctive therapy to treat depression. See U.S. Pat. No. 8,729,120, incorporated by reference herein in its entirety. In some embodiments, APC is administered to a subject in conjunction with an antidepressant such as, without limitation, fluoxetine, amitriptyline, clomipramine, doxepin, imipramine, trimipramine or a pharmaceutically acceptable salt thereof.

In some embodiments, APC may be used to treat fibromyalgia syndrome. See U.S. Pat. Nos. 8,927,602 and 9,688,620; incorporated by reference herein in their entirety.

In some embodiments, APC may be used to treat attention deficit/hyperactivity disorder (ADHD) or diminish symptoms associated with ADHD. See U.S. Pat. Nos. 8,895,609; 9,663,455; and 10,202,335; incorporated by reference herein in their entirety.

In some embodiments, APC may be used to treat restless legs syndrome. See U.S. Pat. No. 8,623,913, incorporated by reference herein in its entirety.

In some embodiments, APC may be used to treat bipolar disorder. See U.S. Pat. Nos. 9,610,274 and 9,907,777; incorporated by reference herein in their entirety. In some embodiments, APC may be used to diminish manic symptoms in a subject suffering from bipolar disorder.

In some embodiments, APC may be used to treat cataplexy. See U.S. Pat. Nos. 9,359,290; 9,585,863; and 10,259,780; incorporated by reference herein in their entirety. In some embodiments, the cataplexy is secondary to a condition that lowers hypocretin levels in a subject, such as a brain tumor, astrocytoma, glioblastoma, glioma, subependynoma, craniopharyngioma, arterio-venous malformations, ischemic events, multiple sclerosis, head injury, brain surgery, paraneoplastic syndromes, Neimann-Pick type C disease, or encephalitis.

In some embodiments, APC may be used to treat obesity, reduce body weight, reduce or prevent body weight gain, reduce food intake, or treat pathological eating. See U.S. Pat. Nos. 9,226,910; 9,649,291; and 10,105,341; incorporated by reference herein in their entirety.

In some embodiments, APC may be used to promote cessation or reduction in the smoking and/or chewing of tobacco or nicotine-containing products and/or to prevent relapse of the same. See US Publication No. 2015/0018414, incorporated by reference herein in its entirety.

Methods of Treating Excessive Daytime Sleepiness

Provided according to embodiments of the present invention are methods of treating excessive daytime sleepiness in a renally impaired subject in need thereof, comprising administering to the subject an APC salt, such as APC-HCl. In some embodiments, such methods comprise administering to the subject an APC salt at an initial dose equivalent to 37.5 mg APC once daily, wherein the subject has an eGFR of 30-59 ml/min/1.73 m$^2$, thereby treating excessive daytime sleepiness in the subject. In particular embodiments, such methods further include increasing the dose to a maximum equivalent of 75 mg APC once daily after at least 7 days. In some embodiments of the invention, the subject has narcolepsy, OSA, or both.

Further provided according to some embodiments of the invention are methods of treating excessive daytime sleepiness in a renally impaired subject in need thereof that comprise administering to the subject an APC salt, such as APC-HCl, at a maximum dose equivalent to 37.5 mg APC once daily; wherein the subject has an eGFR of 15-29 ml/min/1.73 m$^2$; thereby treating excessive daytime sleepiness in the subject.

Further provided according to embodiments of the invention are methods of guiding the treatment of excessive daytime sleepiness in a renally impaired subject in need thereof, comprising:
  (a) determining if the subject has mild renal impairment (an eGFR of 60-89 ml/min/1.73 m$^2$), moderate renal impairment (an eGFR of 30-59 ml/mm/1.73 m$^2$), severe renal impairment (an eGFR of 15-29 ml/min/1.73 m$^2$), or end stage renal disease (an eGFR of <15 ml/min/1.73 m$^2$); and
  (b) administering to the subject the dose of an APC salt (e.g., APC-HCl) recommended for subjects without renal impairment if the subject has mild renal impairment; or administering to the subject an APC salt at an initial dose equivalent to 37.5 mg APC once daily and a maximum dose equivalent to 75 mg APC once daily if the subject has moderate renal impairment; or administering to the subject an APC salt at a maximum dose equivalent to 37.5 mg APC once daily if the subject has severe renal impairment; or not administering to the subject an APC salt if the subject has end stage renal disease.

In some embodiments, the methods further comprise measuring the eGFR in the subject prior to step (a).

Also provided according to other embodiments of the present invention are methods of reducing toxicity of an APC salt (e.g., APC-HCl) in a renally impaired subject, comprising administering to the subject the APC salt at an initial dose equivalent to 37.5 mg APC once daily, wherein the subject has an eGFR of 30-59 ml/min/1.73 m$^2$, thereby reducing toxicity of the APC salt. In particular embodiments, such methods further include increasing the dose to a maximum equivalent of 75 mg APC once daily after at least 7 days. "Reducing toxicity," as used herein, refers to reducing the number and/or severity of adverse reactions or effects associated with APC-HCl therapy relative to the number and/or severity of adverse reactions or effects in the absence of the methods of the invention.

Provided according to some embodiments of the present invention are methods of reducing toxicity of an APC salt (e.g., APC-HCl) in a renally impaired subject, such methods comprising administering to the subject an APC salt at a maximum dose equivalent to 37.5 mg APC once daily, wherein the subject has an eGFR of 15-29 ml/min/1.73 m$^2$, thereby reducing the toxicity of the APC salt in the subject.

Further, provided according to embodiments of the present invention are methods of reducing toxicity of an APC salt in a renally impaired subject, comprising:
  (a) determining if the subject has mild renal impairment (an eGFR of 60-89 ml/min/1.73 m$^2$), moderate renal impairment (an eGFR of 30-59 ml/mm/1.73 m$^2$), severe renal impairment (an eGFR of 15-29 ml/min/1.73 m$^2$), or end stage renal disease (an eGFR of <15 ml/min/1.73 m$^2$); and
  (b) administering to the subject the dose of an APC salt recommended for subjects without renal impairment if the subject has mild renal impairment; or administering to the subject an APC salt at an initial dose equivalent to 37.5 mg APC once daily and a maximum dose equivalent to 75 mg APC once daily if the subject has moderate renal impairment; or administering to the subject an APC salt at a maximum dose equivalent to 37.5 mg APC once daily if the subject has severe renal impairment; or not administering to the subject an APC salt if the subject has end stage renal disease. In some embodiments, the methods further comprise measuring the estimated glomerular filtration rate in the subject prior to step (a).

The methods of the invention may be used to treat any disorder or condition amenable to treatment with APC. Disorders amenable to treatment with APC include, without limitation, excessive daytime sleepiness, fatigue, sleep apnea, drug addiction, sexual dysfunction, depression, fibromyalgia syndrome, attention deficit/hyperactivity disorder, restless legs syndrome, bipolar disorder, cataplexy, obesity, as well as induction of smoking cessation.

Excessive Daytime Sleepiness

"Excessive daytime sleepiness" or "EDS" refers to persistent sleepiness at a time when the individual would be expected to be awake and alert, even during the day after apparently adequate or even prolonged nighttime sleep. EDS may be the result of a sleep disorder or a symptom of another underlying disorder such as narcolepsy, sleep apnea, circadian rhythm sleep disorder, or idiopathic hypersomnia. While the name includes "daytime," it is understood that the sleepiness may occur at other times that the subject should be awake, such as nighttime or other times, e.g., if the subject is working nightshift.

In some embodiments of the invention, treating excessive daytime sleepiness in a subject in need thereof may result in the decrease the subject's score on the Epworth Sleepiness Scale (ESS) by 5 or more points, e.g., by 10 or more points, e.g., by 1, 2, 3, 4, 5, 6, 7, 8, 9, 10, 11, 12, 13, 14, 15, 16, 17, 18, 19, or 20 or more points or any range therein. In some embodiments, the amount of APC salt administered is sufficient to decrease the subject's score on the ESS to a level that is considered normal, e.g., 10 or less. In certain embodiments, at least about 5% of the treated subjects achieve the specified score, e.g., at least about 5%, 10%, 15%, 20%, 25%, 30%, 35%, 40%, 45%, 50%, 55%, 60%, 65%, 70%, 75%, 80%, 85%, 90%, 95%, or more.

The ESS is a subjective sleepiness test that is well known in the art and routinely used to measure the sleepiness level of a subject. The scale is intended to measure daytime sleepiness through the use of a short questionnaire that asks the subject to rate his or her probability of falling asleep on a scale of increasing probability from 0 to 3 for eight different situations that most people engage in during their daily lives. The scores for the eight questions are added together to obtain a single number that estimates the subject's average sleep propensity (ASP). A number in the 0-10 range is considered to be normal while 11-12 indicates mild excessive sleepiness, 13-15 indicates moderate excessive sleepiness, and 16 or higher indicates severe excessive sleepiness. Narcolepsy patients have an average score of about 17. Obstructive sleep apnea (OSA) patients with excessive sleepiness have an average score of about 15.

In some cases, treating excessive daytime sleepiness in a subject in need thereof results in an increase the subject's score on the maintenance of wakefulness test (MWT) by at least 5 minutes, e.g., at least 10 minutes or 15 minutes, e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes or more or any range therein. In certain embodiments, at least about 5% of the treated subjects achieve the specified score, e.g., at least about 5%, 10%, 15%, 20%, 25%, 30%, 35%, 40%, 45%, 50%, 55%, 60%, 65%, 70%, 75%, 80%, 85%, 90%, 95%, or more.

The MWT is an objective test used to measure how alert a subject is during the day. The test consists of four sleep trials with two hours in between the trials. The first trial is performed 1.5-3 hours after the subject's normal wake-up time. Sensors are placed on the head, face, and chin to detect when the subject is asleep and awake during the test. The subject sits quietly in bed with his or her back and head supported by a pillow and is asked to sit still and look straight ahead while trying to stay awake as long as possible. Each trial lasts 40 minutes or until the subject is asleep for 90 seconds. Between trials, the subject stays out of bed and occupies himself or herself to remain awake. Falling asleep in an average of less than eight minutes is considered abnormal. About 40-60% of subjects with normal sleep stay awake for the entire 40 minutes of all four trials.

The baseline measurement for determining a change in test results, such as ESS and MWT, may be performed before the subject has been administered APC or at a timepoint during a course of treatment of APC at which a baseline determination is desired. One or more subsequent determinations of test results may be made at any time after administration of one or more doses of APC. For example, determination of a change in test results may be made 1, 2, 3, 4, 5, or 6 days or 1, 2, 3, 4, 5, 6, 7, 8, 9, or 10 weeks after the administration of APC has begun or after the baseline determination was made.

The methods of the invention may be effective no matter the cause of the EDS, but in some embodiments of the invention, the EDS is associated with narcolepsy or obstructive sleep apnea (OSA). In other embodiments, the cause of the EDS may be, without limitation, central nervous system (CNS) pathologic abnormalities, stroke, idiopathic CNS hypersomnia; sleep deficiency, other sleep apnea, insufficient nocturnal sleep, chronic pain, acute pain, Parkinson's disease, urinary incontinence, multiple sclerosis fatigue, attention deficit hyperactivity disorder (ADHD), Alzheimer's disorder, major depression, bipolar disorder, cardiac ischemia; misalignments of the body's circadian pacemaker with the environment, jet lag, shift work, or sedating drugs.

The methods of the invention may also be used to increase wakefulness and/or alertness in a subject in need thereof.

Renal Impairment

In embodiments of the present invention, the renal status of the subject may be determined by measuring the "estimated glomerular filtration rate" or "eGFR" of the individual. The eGFR in mL/min/1.73 m² is calculated by the Modification of Diet in Renal Disease [MDRD] equation:

$$\text{(eGFR in mL/min)/1.73 m}^2 = 175 \times \text{(serum creatinine in mg/dL)}^{-1.154} \times \text{Age}^{-0.203} \times 0.742 \text{ (if female)} \times 1.212 \text{ (if black)}.$$

Further details regarding the calculation of the eGFR may be found in, e.g., Levey A S, Coresh J, Greene T, Marsh J, Stevens L A, Kusek J W, Van Lente F: Chronic Kidney Disease Epidemiology Collaboration. Expressing the Modification of Diet in Renal Disease Study Equation for Estimating Glomerular Filtration Rate with Standardized Serum Creatinine Values. Ann Intern Med. 2009; 150(9):604-12.

Renal impairment status based on Food and Drug Administration (FDA) guidance is as follows.

Normal: eGFR≥90 mL/min/1.73 m²

Mild: eGFR 60-89 mL/min/1.73 m² (i.e., ≥60 to <90)

Moderate: eGFR 30-59 mL/min/1.73 m$^2$ (i.e., ≥30 to <60)
Severe: eGFR 15-29 mL/min/1.73 m$^2$ (i.e., ≥15 to <30) and not on hemodialysis
End-stage renal disease (ESRD): eGFR<15 mL/min/1.73 m$^2$ and not on hemodialysis or on hemodialysis See, Guidance for Industry Pharmacokinetics in Patients with Impaired Renal Function—Study Design, Data Analysis and Impact on Dosing and Labeling. U.S. Department of Health and Human Services Food and Drug Administration Center for Drug Evaluation and Research (CDER) Center for Biologics Evaluation and Research (CBER) February 2010. As used herein, a "renally impaired subject" may have mild, moderate, or severe renal impairment, or may have ESRD.

APC Salts

The methods of the present invention may be carried out using compounds, formulations and unit dosage forms provided herein. In some embodiments, the formulations and dosage forms may include pharmaceutically acceptable salts of APC ("APC salt"), which also includes hydrates, solvates, clathrates, inclusion compounds, and complexes thereof.

In some embodiments of the invention, the APC salt is a hydrochloride salt (APC-HCl). However, suitable salts of APC also include, without limitation, acetate, adipate, alginate, aspartate, benzoate, butyrate, citrate, fumarate, glycolate, hemisulfate, heptanoate, hexanoate, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compound of the invention and their pharmaceutically acceptable acid addition salts. APC salts include those having quaternization of any basic nitrogen-containing group therein.

The discussion herein is, for simplicity, provided without reference to the addition of deuterium atoms, but the APC salts may further include non-ordinary isotopes. Those skilled in the art will appreciate that the APC salt can contain one or more asymmetric centers and thus occur as racemates and racemic mixtures and single optical isomers. In embodiments of the present invention, the APC salt stereoisomer is preferred, but formulations according to embodiments of the invention may include both (R) and (S) isomers in a racemic mixture, or in any ratio of the isomers. In particular embodiments, the (R)-2-amino-3-phenylpropyl carbamate salt stereoisomer is present at a greater concentration than the (S)-2-amino-3-phenylpropyl carbamate salt stereoisomer, and in some embodiments, the formulation includes the 2-amino-3-phenylpropyl carbamate salt as a substantially enantiomerically pure (R)-2-amino-3-phenylpropyl carbamate salt stereoisomer such as having an enantiomeric excess of greater than 80%, 90%, 95%, or 99%. In some embodiments, the (R)-2-amino-3-phenylpropyl carbamate salt is enantiomerically pure, and in some cases is enantiomerically pure (R)-2-amino-3-phenylpropyl carbamate hydrochloride. When the (R)-2-amino-3-phenylpropyl carbamate salt is referenced specifically, it is understood that the dosage (e.g., 37.5 mg or 75 mg) refers to the equivalent weight of the (R) enantiomer only.

The APC salt(s) may be obtained or synthesized by methods known in the art and as described herein. Details of reaction schemes for synthesizing APC have been described in U.S. Pat. Nos. 5,705,640; 5,756,817; 5,955,499; and 6,140,532, all incorporated herein by reference in their entirety.

APC Salt Formulations

Any suitable dosage form comprising the APC salts may be used in the methods of the invention. In some embodiments, the dosage formulation comprises the APC salt (which is pharmaceutically acceptable) and a pharmaceutically acceptable carrier. In some embodiments, the dosage form is an oral dosage form, e.g., a tablet or a capsule, e.g., an immediate release dosage form.

In some embodiments, the dosage form is an immediate release tablet that releases at least 85%, e.g., at least 85%, 90%, 95%, 96%, 97%, 98%, or 99%, of the APC salt contained therein within a period of less than 15 minutes after administration of the tablet to a subject. See, for example, U.S. Pat. No. 10,195,151, incorporated herein by reference in its entirety.

Formulations of the APC salt, including immediate release formulations, may be processed into unit dosage forms suitable for oral administration, such as for example, filled capsules, compressed tablets or caplets, or other dosage form suitable for oral administration using conventional techniques Immediate release dosage forms prepared as described may be adapted for oral administration, so as to attain and maintain a therapeutic level of the compound over a preselected interval. In certain embodiments, an immediate release dosage form as described herein may comprise a solid oral dosage form of any desired shape and size including round, oval, oblong cylindrical, or polygonal. In one such embodiment, the surfaces of the immediate release dosage form may be flat, round, concave, or convex. In some embodiments, the shape may be selected to maximize surface area, e.g., to increase the rate of dissolution of the dosage form.

In particular, when the immediate release formulations are prepared as a tablet, the immediate release tablets may contain a relatively large percentage and absolute amount of the compound and so may be expected to improve patient compliance and convenience by replacing the need to ingest large amounts of liquids or liquid/solid suspensions. One or more immediate release tablets as described herein can be administered, by oral ingestion, e.g., closely spaced, in order to provide a therapeutically effective dose of the compound to the subject in a relatively short period of time.

Where desired or necessary, the outer surface of an immediate release dosage form may be coated, e.g., with a color coat or with a moisture barrier layer using materials and methods known in the art.

In some embodiments, the dosage formulation is an immediate release compressed tablet, the tablet comprising: the APC salt thereof in an amount of about 90-98% by weight of the tablet; at least one binder in an amount of about 1-5% by weight of the tablet; and at least one lubricant in an amount of about 0.1-2% by weight of the tablet; wherein the tablet releases at least 85% of the APC or a pharmaceutically acceptable salt thereof contained therein within a period of less than 15 minutes after administration of the tablet to a subject.

In one embodiment, the tablet comprises: the APC salt thereof in an amount of about 91-95% by weight of the tablet; at least one binder in an amount of about 2-3% by weight of the tablet; at least one lubricant in an amount of about 0.1-1% by weight of the tablet; and optionally, a cosmetic film coat in an amount of about 3-4% by weight of the tablet; wherein the tablet releases at least 85% of the APC or a pharmaceutically acceptable salt thereof contained therein within a period of less than 15 minutes after administration of the tablet to a subject.

In one embodiment, the tablet comprises: the APC salt thereof in an amount of about 93.22% by weight of the tablet; at least one binder (e.g., hydroxypropylcellulose) in an amount of about 2.87% by weight of the tablet; at least one lubricant (e.g., magnesium stearate) in an amount of about 0.52% by weight of the tablet; and optionally, a cosmetic film coat (e.g., Opadry® II yellow) in an amount of about 3-4% by weight of the tablet; wherein the tablet releases at least 85% of the APC salt thereof contained therein within a period of less than 15 minutes after administration of the tablet to a subject.

In some embodiments, the composition is an immediate release oral dosage form of an APC salt, the oral dosage form comprising: the APC salt thereof in an amount of about 90-98% by weight of the oral dosage form; at least one binder in an amount of about 1-5% by weight of the oral dosage form; and at least one lubricant in an amount of about 0.1-2% by weight of the oral dosage form; wherein the oral dosage form releases at least 85% of the APC salt thereof contained therein within a period of less than 15 minutes after administration of the oral dosage form to a subject.

In certain embodiments, the tablet does not comprise a disintegrant. The term "disintegrant," as used herein, refers to an agent added to a tablet to promote the breakup of the tablet in an aqueous environment. The tablets of the present invention are advantageous in that they dissolve rather than disintegrate. In the present invention the presence of disintegrant in the formulation may actually slow down release of APC.

In certain embodiments, the APC salt is present in an amount of about 90%, 90.5%, 91%, 91.5%, 92%, 92.5%, 93%, 93.5%, 94%, 94.5%, 95%, 95.5%, 96%, 96.5%, 97%, 97.5%, or 98% by weight of the tablet or any value or range therein. In certain embodiments, the APC salt thereof is present in an amount of about 90% to about 98%, about 92% to about 98%, about 94% to about 98%, about 96% to about 98%, about 90% to about 92%, about 90% to about 94%, about 90% to about 96%, about 92% to about 94%, about 92% to about 96%, or about 94% to about 96%.

In certain embodiments, the at least one binder is present in an amount of about 1%, 1.5%, 2%, 2.5%, 3%, 3.5%, 4%, 4.5%, or 5% by weight of the tablet or any value or range therein. In certain embodiments, the at least one binder is present in an amount of about 1% to about 5%, about 2% to about 5%, about 3% to about 5%, about 4% to about 5%, about 1% to about 2%, about 1% to about 3%, about 1% to about 4%, about 2% to about 3%, about 2% to about 4%, or about 3% to about 4%. The tablet may comprise at least one binder, e.g., 1, 2, 3, 4, 5, or more binders.

In certain embodiments, the at least one binder is selected from at least one of hydroxypropyl cellulose, ethylcellulose, hydroxypropyl methylcellulose, polyvinyl alcohol, hydroxyethyl cellulose, povidone, copovidone, pregelatinized starch, dextrin, gelatin, maltodextrin, zein, acacia, alginic acid, carbomers (cross-linked polyacrylates), polymethacrylates, sodium carboxymethylcellulose, guar gum, hydrogenated vegetable oil (type 1), methylcellulose, magnesium aluminum silicate, and sodium alginate or any combination thereof. In some embodiments, the at least one binder is hydroxypropyl cellulose.

In certain embodiments, the at least one lubricant is present in an amount of about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0% by weight of the tablet or any value or range therein. In certain embodiments, the at least one lubricant is present in an amount of about 0.1% to about 2.0%, about 0.5% to about 2.0%, about 1.0% to about 2.0%, about 1.5% to about 2.0%, about 0.1% to about 0.5%, about 0.1% to about 1.0%, about 0.1% to about 1.5%, about 0.5% to about 1.0%, about 0.5% to about 1.5%, or about 1.0% to about 1.5%. The tablet may comprise at least one lubricant, e.g., 1, 2, 3, 4, 5, or more lubricants. Where the immediate release formulation is provided as a tableted dosage form, still lower lubricant levels may be achieved with use of a "puffer" system during tableting. Such systems are known in the art, commercially available and apply lubricant directly to the punch and die surfaces rather than throughout the formulation.

In certain embodiments, the at least one lubricant is selected from at least one of magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, and zinc stearate or any combination thereof. In some embodiments, the at least one lubricant is magnesium stearate. In other embodiments, magnesium stearate may be used in combination with one or more other lubricants or a surfactant, such as sodium lauryl sulfate. In particular, if needed to overcome potential hydrophobic properties of magnesium stearate, sodium lauryl sulfate may also be included when using magnesium stearate (Remington: the Science and Practice of Pharmacy, 20th edition, Gennaro, Ed., Lippincott Williams & Wilkins (2000)).

In some embodiments, the at least one binder is hydroxypropyl cellulose. In some embodiments, the at least one lubricant is magnesium stearate. In some embodiments, the at least one binder is hydroxypropyl cellulose and the at least one lubricant is magnesium stearate.

In certain embodiments, the tablet is coated. The coating may be, without limitation, a color overcoat.

The tablet may be any shape that is suitable for immediate release and allows the release of at least 85% of the APC salt contained therein within a period of less than 15 minutes after administration of the tablet to a subject. In some embodiments, the tablet maximizes surface area to volume ratio to promote rapid dissolution. In some embodiments, the tablet is oblong in shape.

The tablet may contain any amount of the APC salt suitable for administration as a unit dosage form. In some embodiments, the tablet contains the equivalent of about 1 mg to about 1000 mg of APC or any range or value therein, e.g., about 100 mg to about 500 mg, e.g., about 37.5 mg, about 75 mg, about 150 mg, or about 300 mg.

["Immediate release" as used herein, refers to a composition that releases the APC salt substantially completely into the gastrointestinal tract of the user within a period of less than about 15 minutes, usually between about 1 minute and about 15 minutes from ingestion. Such a delivery rate allows the drug to be absorbed by the gastrointestinal tract in a manner that is bioequivalent to an oral solution. Such rapid absorption will typically occur for an immediate release unit dosage form, such as a tablet, caplet or capsule, if the drug included in such dosage form dissolves in the upper portion the gastrointestinal tract.

Release rates can be measured using standard dissolution test methods. For example, the standard conditions may be those described in FDA guidance (e.g., 50 rpm, 37° C., USP 2 paddles, pH 1.2 and pH 6.8 media, 900 ml, 1 test article per vessel).

Immediate release formulations suitable for oral administration may comprise unit dosage forms, such as tablets, caplets or filled capsules, which can deliver a therapeutically effective dose of the APC salt upon ingestion thereof by the patient of one or more of said dosage forms, each of which can provide a dosage of, for example, about 37.5 mg to about 75 mg, or 75 mg to about 150 mg of APC. Additionally, the immediate release dosage forms can be shaped or scored to facilitate dose adjustment through tablet splitting. For example, a 75 mg APC tablet or caplet may be scored to facilitate tablet splitting into two 37.5 mg APC doses.

The formulation and structure of an immediate release dosage form as disclosed herein can be adjusted to provide immediate release performance that suits a particular dosing need. In particular, the formulation and structure of the dosage forms as described herein can be adjusted to provide any combination of the immediate release performance characteristics described herein. In particular embodiments, for example, an immediate release dosage form as disclosed herein provides rapid onset of action, releasing more than about 85%, such as, for example, more than about 90% or 95%, of the drug contained therein within a period of time selected from less than 15 minutes, less than 12 minutes, less than 10 minutes, and less than 5 minutes after administration.

Moreover, the rate of drug release from an immediate release dosage form as disclosed herein may be adjusted as needed to facilitate a desired dosing regimen or achieve targeted dosing. In certain such embodiments, the total amount of the APC salt in the dosage formulation may include an equivalent dose of about 10 mg to about 300 mg APC, about 30 mg to about 300 mg APC, about 100 mg to about 300 mg APC, or about 150 mg to about 300 mg APC, about 75 to 150 mg APC, about 37.5 to about 75 mg APC, and about 37.5 to about 150 mg APC. In particular embodiments, the equivalent dose of APC in the dosage formulation is 37.5 mg, and in other particular embodiments, the equivalent dose of APC in the dosage formulation is 75 mg. In some cases, such dosage formulations may be formed (e.g., scoring) to facilitate creating more than one dose from a particular dosage form.

The immediate release formulations provided herein generally include the APC salt and some level of lubricant to facilitate processing of the formulations into a unit dosage form. In some embodiments, therefore, the formulations described herein include a combination of the APC salt and lubricant, as described herein, and in certain such embodiments, the immediate release formulations are substantially free of other excipients or adjuvants. In other embodiments, the immediate release formulations described herein include a combination of the APC salt, lubricant, and binder, as described herein, and in certain such embodiments, the immediate release formulations are substantially free of other excipients or adjuvants. Though the immediate release formulations described herein may be formulated using a combination of drug and one or more of a lubricant and binder, in certain embodiments, the compositions described herein may include one or more additional excipients selected from, for example, fillers, compression aids, diluents, disintegrants, colorants, flavorants, buffering agents, coatings, glidants, or other suitable excipients.

The immediate release formulations described herein may be manufactured using standard techniques, such as wet granulation, roller compaction, fluid bed granulation, and dry powder blending. Suitable methods for the manufacture of the immediate release formulations and unit dosage forms described herein are provided, for example, in Remington, 20th edition, Chapter 45 (Oral Solid Dosage Forms). It has been found that, even without the aid of binders or non-lubricating excipients, such as compression aids, wet granulation techniques can afford flowable granules with compression characteristics suitable for forming unit dosage forms as described herein. Therefore, in certain embodiments, where a drug content greater than about 85%, 90% or 95% by weight is desired for the immediate release formulation, wet granulation techniques may be used to prepare immediate release formulations as described herein. In such embodiments, as illustrated in the Examples provided herein, conventional organic or aqueous solvents may be used in the wet granulation process. Suitable wet granulation processes can be performed as fluidized bed, high shear, or low shear (wet massing) granulation techniques, as are known in the art.

In addition to one or more the APC salt, lubricant, and binder, where desired, the immediate release formulations described herein may also include fillers or compression aids selected from at least one of lactose, calcium carbonate, calcium sulfate, compressible sugars, dextrates, dextrin, dextrose, kaolin, magnesium carbonate, magnesium oxide, maltodextrin, mannitol, microcrystalline cellulose, powdered cellulose, and sucrose. Where a filler or compression aid is used, in certain embodiments, it may be included in the immediate release formulation in an amount ranging from about 1%-15% by weight.

Where desired or necessary, the outer surface of an immediate release dosage form as disclosed herein may be coated with a moisture barrier layer using materials and methods known in the art. For example, where the APC salt delivered by the unit dosage form is highly hygroscopic, providing a moisture barrier layer over the immediate release dosage form as disclosed herein may be desirable. For example, protection of an immediate release dosage form as disclosed herein from water during storage may be provided or enhanced by coating the tablet with a coating of a substantially water soluble or insoluble polymer. Useful water-insoluble or water-resistant coating polymers include ethyl cellulose and polyvinyl acetates. Further water-insoluble or water resistant coating polymers include polyacrylates, polymethacrylates or the like. Suitable water-soluble polymers include polyvinyl alcohol and HPMC. Further suitable water-soluble polymers include PVP, HPC, HPEC, PEG, HEC and the like.

Where desired or necessary, the outer surface of an immediate release dosage form as disclosed herein may be coated with a color overcoat or other aesthetic or functional layer using materials and methods known in the art.

The dosage forms disclosed herein can also be provided as a kit comprising, separately packaged, a container comprising a plurality of immediate release tablets, which tablets can be individually packaged, as in foil envelopes or in a blister pack. The tablets can be packaged in many conformations with or without desiccants or other materials to prevent ingress of water. Instruction materials or means, such as printed labeling, can also be included for their administration, e.g., sequentially over a preselected time period and/or at preselected intervals, to yield the desired levels of APC in vivo for preselected periods of time, to treat a preselected condition.

Daily Dosage and Treatment Regimens

In the methods described herein, the typical daily dose of the APC salt for subjects with normal renal function, equivalent to 75-150 mg of APC, is modified for certain renally impaired subjects. As discussed above, for a subject with an eGFR of 30-59 ml/min/1.73 m$^2$, i.e., a subject with moderate renal impairment, the APC salt is administered once daily at an initial dose equivalent to 37.5 mg of APC. In some cases, this daily dose may be increased after at least 7 days of the initial dose equivalent to 75 mg of APC. Further, in some embodiments, for a subject with an eGFR of 15-29 ml/min/ 1.73 m$^2$, i.e., a subject with severe renal impairment, the APC salt is administered once daily at a maximum dose equivalent to 37.5 of APC. In some embodiments, such dosages may be used for a subject who has narcolepsy, a subject with OSA, or when reduction of toxicity of the APC salt is indicated. In particular embodiments, the APC salt is APC-HCl.

A dose is "equivalent to" a 37.5 mg or 75 mg of APC, if the weight of the APC base (the "active moiety") in the formulation is 37.5 mg or 75 mg, respectively, regardless of the weight of the APC salt. Thus, the weight of the APC salt may be greater than 37.5 mg or 75 mg, respectively, in the formulation. Where APC is provided in the form of APC-HCl salt, a dose of 37.5 mg APC is equivalent to 44.7 mg (or 44.65 mg) of APC-HCl; a dose of 75 mg APC is equivalent to 89.3 mg of APC-HCl; and a dose of 150 mg APC is equivalent to 178.5 mg of APC-HCl. An "initial dose equivalent" is the daily dose at which the subject starts the treatment regimen, corresponding to the weight of the active moiety (APC), and the initial dose may be increased at some time point, such as in a number of days (e.g., 1, 2, 3, 4, 5, 6, 7, or more days). The "maximum dose equivalent" is the largest dose, corresponding to the weight of the active moiety (APC), that the patient may be administered daily at any time point.

In general, the daily dose is administered once daily. However, in some embodiments, the daily dose may be administered at two or more different time points. Administration of the APC salt can continue for one, two, three, four, five, six, seven, eight, nine, ten, eleven, or twelve weeks or longer. Alternatively, administration of the APC salt can continue for one, two, or three months, or longer. Optionally, after a period of rest, the compound can be administered under the same or a different schedule. The period of rest can be one, two, three, or four weeks, or longer, according to the pharmacodynamic effects of the compound on the subject. In another embodiment, the compound can be administered to build up to a certain level, then maintained at a constant level and then a tailing dosage.

In one aspect of the invention, the APC salt is delivered to a subject concurrently with an additional therapeutic agent. The additional therapeutic agent can be delivered in the same composition as the compound or in a separate composition. The additional therapeutic agent can be delivered to the subject on a different schedule or by a different route as compared to the compound. The additional therapeutic agent can be any agent that provides a benefit to the subject. Such agents include, without limitation, stimulants, anti-psychotics, anti-depressants, agents for neurological disorders, and chemotherapeutic agents. In some embodiments, the APC salt is delivered to a subject concurrently with an additional therapeutic agent that is not a monoamine oxidase inhibitor. In still other embodiments, the APC salt is delivered to a subject who has not been treated with a monoamine oxidase inhibitor within the preceding 14 days. In exemplary embodiments of the invention, a subject with obstructive sleep apnea is treated with APC concurrently with adherence to a primary OSA therapy. Examples of primary OSA therapies include, without limitation, positive airway pressure (PAP), continuous positive airway pressure (CPAP), oral appliances, and surgical procedures. One therapeutic agent that can be administered during the same period is Xyrem®, sold commercially by Jazz Pharmaceuticals, which is used to treat narcolepsy and cataplexy. See U.S. Pat. Nos. 8,952,062 and 9,050,302.

The APC salt can be administered at any time during the day, but in some embodiments, the APC salt is administered to the subject no later than at least 12 hours before the bedtime of the subject. Studies by the present inventors have found that that administration of the APC salt within a few of hours of waking minimizes side effects of the treatment such as insomnia. In some embodiments, the APC is administered shortly after waking, e.g., within about 0.25, 0.5, 0.75, 1, 1.5, 2, 2.5, or 3 hours of waking. In exemplary embodiments, the APC is administered at least 9 hours before the bedtime of the subject, e.g., at least 9, 10, 11, 12, 13, 14, 15, or 16 or more hours before bedtime.

Subjects

The present invention finds use in research as well as veterinary and medical applications. Suitable subjects are generally mammalian subjects. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects. In some embodiments of the invention, the human subject is an adult.

In particular embodiments, the subject is a human subject that has excessive daytime sleepiness or another disorder amenable to treatment with the APC salt. In other embodiments, the subject used in the methods of the invention is an animal model of excessive daytime sleepiness or another disorder amenable to treatment with APC.

The subject can be a subject "in need of" the methods of the present invention, e.g., in need of the therapeutic effects of the inventive methods. For example, the subject can be a subject that is experiencing excessive daytime sleepiness or another disorder or condition amenable to treatment with APC, is suspected of having excessive daytime sleepiness or another disorder or condition amenable to treatment with APC, and/or is anticipated to experience excessive daytime sleepiness or another disorder or condition amenable to treatment with APC, and the methods and compositions of the invention are used for therapeutic and/or prophylactic treatment. Disorders amenable to treatment with APC include, without limitation, sleep-wake disorder, excessive daytime sleepiness, depression, attention deficit/hyperactivity disorder, drug addiction, bipolar disorder, fibromyalgia, fatigue, obesity, restless legs syndrome, cataplexy, and sexual dysfunction.

Specific embodiments of the invention include, without limitation, the following.

Embodiment 1: A method of providing [R]-2-amino-3-phenylpropylcarbamate hydrochloride (APC-HCl) to a renally impaired subject in need thereof according to a dose escalation regimen, said method comprising
  providing to the subject a first oral daily dose equivalent to 37.5 mg [R]-2-amino-3-phenylpropylcarbamate (APC) from day one to day $n_1$ of the dose escalation regimen; and
  providing to the subject a second oral daily dose equivalent to 75 mg APC starting on day $n_2$ of the dose escalation regimen,
  wherein $n_1$ is an integer equal to or greater than 5 and $n_2$ is equal to the sum of $n_1+1$,
  wherein the renally impaired subject is not provided a daily dose exceeding a dose equivalent to 75 mg APC, and
  wherein the renally impaired subject has an estimated glomerular filtration rate (eGFR) of about 30 mL/min/ 1.73 m$^2$ to about 59 mL/min/1.73 m$^2$.

Embodiment 2: The method of embodiment 1, wherein the subject is provided APC-HCl for the treatment of excessive daytime sleepiness.

Embodiment 3: The method of embodiment 2, wherein the excessive daytime sleepiness is associated with narcolepsy.

Embodiment 4: The method of embodiment 2, wherein the excessive daytime sleepiness is associated with obstructive sleep apnea.

Embodiment 5: The method of embodiment 1, wherein the subject is provided the first oral daily dose in the form of about 44.7 mg APC-HCl.

Embodiment 6: The method of embodiment 1, wherein the subject is provided the second oral daily dose in the form of about 89.3 mg APC-HCl.

Embodiment 7: The method of embodiment 1, wherein the subject is provided a first oral daily dose in the form of about 44.7 mg APC-HCl and a second oral daily dose in the form of about 89.3 mg APC-HCl.

Embodiment 8: The method of embodiment 1, wherein the first oral daily dose and second oral daily dose are each administered upon the subject's awakening.

Embodiment 9: The method of embodiment 1, wherein the first oral daily dose and second oral daily dose are each administered more than nine hours in advance of the subject's bedtime.

Embodiment 10: The method of embodiment 1, wherein the subject is a human.

Embodiment 11: The method of embodiment 1, wherein the eGFR is determined using the Modification in Diet in Renal Disease equation.

Embodiment 12: The method of embodiment 1, wherein $n_1$ is an integer equal to or greater than 7.

Embodiment 13: A method of providing APC-HCl to a renally impaired subject with narcolepsy in need thereof, said method comprising:
  providing to the subject an oral daily dose equivalent to 37.5 mg APC,
  wherein the renally impaired subject is not provided a daily dose exceeding a dose equivalent to 37.5 mg APC; and
  wherein the renally impaired subject has an eGFR of about 15 ml/min/1.73 m$^2$ to about 29 ml/min/1.73 m$^2$.

Embodiment 14: The method of embodiment 13, wherein the oral daily dose is provided to the renally impaired subject in the form of 44.7 mg APC-HCl.

Embodiment 15: The method of embodiment 13, wherein the oral daily dose is administered upon the subject's awakening.

Embodiment 16: The method of embodiment 13, wherein the oral daily dose is administered more than nine hours in advance of the subject's bedtime.

Embodiment 17: The method of embodiment 13, wherein the subject is a human.

Embodiment 18: The method of embodiment 17, wherein the subject is an adult.

Embodiment 19: The method of embodiment 13, wherein the eGFR is determined using the Modification in Diet in Renal Disease equation.

Embodiment 20: A method of treating excessive daytime sleepiness in a renally impaired subject with narcolepsy in need thereof, comprising administering to the subject APC-HCl at an initial dose equivalent to 37.5 mg APC once daily;
  wherein the subject has an eGFR of 30-59 ml/min/1.73 m$^2$; thereby treating excessive daytime sleepiness in the subject.

Embodiment 21: The method of embodiment 20, further comprising increasing the dose to a maximum equivalent to 75 APC once daily after at least 5 days.

Embodiment 22: The method of embodiment 21, wherein the dose is increased to a maximum equivalent to 75 mg APC once daily after at least 7 days.

Embodiment 23: A method of treating excessive daytime sleepiness in a renally impaired subject with narcolepsy in need thereof, comprising administering to the subject APC-HCl at a maximum dose equivalent to 37.5 mg APC once daily;
  wherein the subject has an eGFR of 15-29 ml/min/1.73 m$^2$; thereby treating excessive daytime sleepiness in the subject.

Embodiment 24: A method of guiding APC therapy in a renally impaired subject with narcolepsy in need thereof, comprising
  a. determining if the subject has mild renal impairment (an eGFR of 60-89 ml/min/1.73 m$^2$), moderate renal impairment (an eGFR of 30-59 ml/min/1.73 m$^2$), severe renal impairment (an eGFR of 15-29 ml/min/1.73 m$^2$), or end stage renal disease (an eGFR of less than 15 ml/min/1.73 m$^2$); and
  b. administering to the subject APC-HCl according to a regimen recommended for subjects without renal impairment if the subject has mild renal impairment, said regimen comprising an initial dose equivalent to 75 mg APC once daily and a maximum dose equivalent to 150 mg APC once daily; or
  administering to the subject APC-HCl at an initial dose equivalent to 37.5 mg APC once daily and a maximum dose equivalent to 75 mg APC once daily if the subject has moderate renal impairment; or
  administering to the subject APC-HCl at a maximum dose equivalent to 37.5 mg APC once daily if the subject has severe renal impairment; or
  not administering to the subject APC-HCl if the subject has end stage renal disease.

Embodiment 25: The method of embodiment 24, further comprising measuring the eGFR in the subject prior to step a.

Embodiment 26: The method of embodiment 24, wherein the dose is increased from a dose equivalent to 75 mg APC to a dose equivalent to 150 mg APC after at least 3 days if the subject has mild renal impairment and the dose is increased from a dose equivalent to 37.5 mg APC to a dose equivalent to 75 mg APC after at least 7 days if the subject has moderate renal impairment.

Embodiment 27: A method of guiding APC therapy in a renally impaired subject with obstructive sleep apnea in need thereof, comprising:
  a. determining if the subject has mild renal impairment (an eGFR of 60-89 ml/min/1.73 m$^2$), moderate renal impairment (an eGFR of 30-59 ml/min/1.73 m$^2$), severe renal impairment (an eGFR of 15-29 ml/min/1.73 m$^2$), or end stage renal disease (an eGFR of less than 15 ml/min/1.73 m$^2$); and
  b. administering to the subject APC-HCl according to a regimen recommended for subjects without renal impairment if the subject has mild renal impairment, said regimen comprising an initial dose equivalent to 37.5 mg APC once daily and a maximum dose equivalent to 150 mg APC once daily;
  or administering to the subject APC-HCl at an initial dose equivalent to 37.5 mg APC once daily and a maximum dose equivalent to 75 mg APC once daily if the subject has moderate renal impairment; or administering to the subject APC-HCl at a maximum dose equivalent to 37.5 mg APC once daily if the subject has severe renal impairment; or not administering to the subject APC-HCl if the subject has end stage renal disease.

Embodiment 28: The method of embodiment 27, further comprising measuring the eGFR in the subject prior to step a.

Embodiment 29: The method of embodiment 27, wherein the regimen comprises doubling the dose of APC-HCl at intervals of at least 3 days if the subject has mild renal impairment and increasing the dose from a dose equivalent to 37.5 mg APC to a dose equivalent to 75 mg APC after at least 7 days if the subject has moderate renal impairment.

Embodiment 30: A method of treating excessive daytime sleepiness in a renally impaired subject with obstructive sleep apnea in need thereof, comprising administering to the subject APC-HCl at an initial dose equivalent to 37.5 mg APC once daily, wherein the subject has an eGFR of 30-59 ml/min/1.73 m$^2$, thereby treating excessive daytime sleepiness in the subject.

Embodiment 31: The method of embodiment 30, wherein the dose is increased to a maximum equivalent to 75 mg APC once daily after at least 7 days.

Embodiment 32: A method of treating excessive daytime sleepiness in a renally impaired subject with obstructive sleep apnea in need thereof, comprising administering to the subject APC-HCl at a maximum dose equivalent to 37.5 mg APC once daily;

wherein the subject has an eGFR of 15-29 ml/min/1.73 m$^2$, thereby treating excessive daytime sleepiness in the subject.

Embodiment 33: A method of reducing toxicity of APC-HCl therapy in a renally impaired subject, comprising:

administering to the subject APC-HCl at an initial dose equivalent to 37.5 mg APC once daily;

increasing the daily dose to a maximum dose equivalent to 75 mg APC after at least 7 days;

wherein the subject has an eGFR of 30-59 ml/min/1.73 m$^2$, thereby reducing toxicity of APC-HCl therapy in the subject.

Embodiment 34: The method of embodiment 33, wherein the initial dose is provided in the form of about 44.7 mg APC-HCl and the maximum dose is provided in the form of about 89.3 mg APC-HCl.

Embodiment 35: A method of reducing toxicity of APC-HCl therapy in a renally impaired subject, comprising administering to the subject APC-HCl at a maximum dose equivalent to 37.5 mg APC once daily; wherein the subject has an eGFR of 15-29 ml/min/1.73 m$^2$, thereby reducing toxicity of APC-HCl in the subject.

Embodiment 36: The method of embodiment 35, wherein the maximum dose is provided in the form of about 44.7 mg APC-HCl.

Embodiment 37: A method of reducing toxicity of APC-HCl therapy in a renally impaired subject, comprising:

a. determining if the subject has mild renal impairment (an eGFR of 60-89 ml/min/1.73 m$^2$), moderate renal impairment (an eGFR of 30-59 ml/min/1.73 m$^2$), severe renal impairment (an eGFR of 15-29 ml/min/1.73 m$^2$), or end stage renal disease (an eGFR of <15 ml/min/1.73 m$^2$); and b. administering to the subject APC-HCl at a dose of APC-HCl recommended for subjects without renal impairment if the subject has mild renal impairment, wherein the dose of APC-HCl recommended for subjects without renal impairment comprises an initial dose equivalent to 75 mg APC once daily and a maximum dose equivalent to 150 mg APC once daily after at least 3 days; or administering to the subject APC-HCl at an initial dose equivalent to 37.5 mg APC once daily and a maximum dose equivalent to 75 mg APC once daily after at least 7 days if the subject has moderate renal impairment; or administering to the subject APC-HCl at a maximum dose equivalent to 37.5 mg APC1 once daily if the subject has severe renal impairment; or not administering to the subject APC-HCl if the subject has end stage renal disease.

Embodiment 38: The method of embodiment 37, further comprising measuring the eGFR in the subject prior to step a.

Embodiment 39: The method of embodiment 37, wherein the eGFR is calculated by the Modification of Diet in Renal Disease equation.

Embodiment 40: The method of embodiment 37, wherein the subject is a human.

Embodiment 41: The method of embodiment 40, wherein the subject is an adult.

Embodiment 42: The method of embodiment 37, wherein the APC-HCl is administered orally.

Embodiment 43: The method of embodiment 37, wherein the APC-HCl is formulated with a pharmaceutical carrier.

Embodiment 44: The method of embodiment 37, wherein the subject is being treated for excessive daytime sleepiness associated with narcolepsy.

[The present invention is explained in greater detail in the following non-limiting Examples. Each example has a self-contained list of references.

Example 1: Evaluation of the PK of Solriamfetol HCl in Participants with Renal Impairment and Those with ESRD Undergoing Hemodialysis Compared with Healthy Participants with Normal Renal Function Methods In healthy subjects with normal renal function, solriamfetol HCl is renally excreted ~90% unchanged within 48 hours of administration. Thus, renal impairment, as well as hemodialysis in individuals with end-stage renal disease (ESRD), could affect the PK of solriamfetol HCl. To ascertain the precise impact of renal impairment and hemodialysis on pharmacokinetics and safety of solriamfetol HCl, a Phase 1, parallel-group, open-label, single-dose study was conducted at 2 U.S. sites. The protocol was approved by the IntegReview Institutional Review Board (Austin, Texas), and the study was conducted in compliance with the protocol, the Guideline for Good Clinical Practice E6; the US Code of Federal Regulations pertaining to conduct and reporting of clinical studies; the Clinical Trials Directive of the European Medicines Agency (Directive 2001/20/EC); and the Declaration of Helsinki. Written informed consent was obtained from each subject before enrollment in the study and before performance of any study-related procedure. See, also, Zomorodi K, Chen D, Lee L, Lasseter K, Marbury T. An Open-Label, Single-Dose, Phase 1 Study of the Pharmacokinetics and Safety of JZP-110 in Subjects With Normal or Impaired Renal Function and With End-Stage Renal Disease Requiring Hemodialysis [abstract]. *Sleep*. 2017; 40 (suppl): A382-383.

Eligible participants were men and non-pregnant, non-lactating women between the ages of 18 and 80 years, with a body mass index (BMI)≤35 kg/m². Women of childbearing potential were required to have used a medically accepted method of birth control for at least 2 months prior to the first dose of study drug, with continued use throughout the study period and for 30 days after study completion. Participants were excluded if they had a clinically significant medical abnormality (other than renal impairment or its underlying causes), or any unstable conditions including neurological or psychiatric disorder, hepatic, endocrine, cardiovascular, gastrointestinal, pulmonary, or metabolic disease, or any other abnormality that could interfere with the PK evaluation of the study drug or the participant's completion of the trial.

Eligible participants were assigned to 1 of 5 groups according to renal disease status as measured by the estimated glomerular filtration rate (eGFR) on the day prior to dosing, calculated using the Modification in Diet in Renal Disease equation. Group 1 consisted of healthy participants with normal renal function (eGFR≥90 mL/min/1.73 m²) and served as the control group. Groups 2, 3, and 4 had mild, moderate, and severe renal impairment based on eGFRs of 60-89, 30-59, and <30 mL/min/1.73 m², respectively. Group 5 consisted of participants with ESRD who required ≥3 hemodialysis treatments per week for the preceding 3 months. Every effort was made to ensure that the groups were comparable with respect to age, sex, and body mass index (BMI). Group 1 was enrolled last to facilitate matching the mean age, BMI, and sex distribution of Groups 2-5.

Among participants with impaired renal function, continued use of medications necessary for treatment of renal function and/or coexisting disease was allowed, with the exception of monoamine oxidase inhibitors and medications with known risk for torsade de pointes.

Groups 1-4 received one dose of solriamfetol HCl (89.3 mg; equivalent to 75-mg solriamfetol) on day 1; Group 5 received one dose equivalent to 75-mg dose on day 1 followed by 4-hour hemodialysis (designated Group 5.2), and one dose equivalent to 75-mg solriamfetol on day 8 without hemodialysis (designated Group 5.1). All doses were administered on an empty stomach following an overnight fast except for participants in Group 5, who received a standardized snack on day 7 and breakfast early on day 8 before starting an 8-hour fast. Participants remained fasting for 4 hours after administration, with water allowed except for 1 hour before and after dosing.

In this study, 75 mg solriamfetol was selected as the dose for administration in participants with renal impairment as it was considered sufficiently low and potentially safe for this population. The 75-mg dose was expected to result in plasma concentrations of solriamfetol that were above the assay detection level at time points sufficient to characterize the PK profile.

Serial blood samples of approximately 4 mL were collected within 30 minutes prior to dosing and at 0.5, 1, 1.5, 2, 2.5, 3, 4, 6, 8, 10, 12, 24, 36, and 48 hours post-dose in Groups 1-3, with continued sampling at 60 and 72 hours post-dose in Groups 4 and 5. All blood samples were collected into labeled $K_2$EDTA tubes by direct venipuncture or indwelling catheter and kept on ice until the samples were centrifuged within 30 minutes of collection at approximately 2500 rpm (1315×g) at 4° C. for 10 minutes. The plasma was transferred into polypropylene tubes for freezing and storage at −70° C. until analysis.

Urine samples were collected predose and for the time intervals of 0-4, 4-8, 8-12, 12-24, and 24-48 hours in Groups 1-3, with additional collection for the 48-72 hour time interval in Groups 4 and 5. During the hemodialysis period on day 1 for Group 5, dialysate samples and pre- and post-dialyzer paired blood samples were collected at pre-dialysis (2 hours), and at 3, 4, 5, and 6 hours following dosing. Urine and dialysate samples were aliquoted into polypropylene tubes for freezing and storage at −70° C. until analysis. All blood, urine, and dialysate samples were shipped on dry ice to a central bioanalytical laboratory.

Bioanalytical analyses were performed by a central laboratory (KCAS, LLC, Shawnee, Kansas) using validated proprietary methods that included extraction/derivatization and liquid chromatography-tandem mass spectrometry (LC-MS/MS). Measurement of solriamfetol was over the linear range of 8.42 to 4,210 ng/mL in plasma, 0.21 to 84.2 μg/mL in urine, and 1.68 to 842 ng/mL in dialysate. Solriamfetol was removed from dialysate samples with use of the Fresenius Optiflux F180NR dialyzer (Fresenius Medical Care, Waltham, Massachusetts). Assay performance was monitored by spiking blank interference free human plasma with positive controls and internal standards to generate standard curve and quality control samples. After derivatization, samples were chromatographed on a C8 reversed phase analytical HPLC (high-performance liquid chromatography) column, with subsequent monitoring using an API4000 LC-MS/MS unit (Sciex, Framingham, Massachusetts). Quantification was based on setting a calibration graph using the internal standard method. Coefficients of variation (CVs) for quality control samples were 3.2% to 6.0% for the plasma samples, 1.6% to 5.6% for the urine samples, and 3.5% to 7.1% for the dialysate samples.

The following plasma PK parameters were evaluated using non-compartmental analysis in Phoenix® WinNonlin® Version 6.3: $C_{max}$; time to reach $C_{max}$ following drug administration ($t_{max}$); $t_{1/2}$; area under the plasma concentration-time curve from time zero to time of last quantifiable concentration ($AUC_t$); AUC from time zero to infinity ($AUC_\infty$); apparent total clearance of the drug from plasma after oral administration (CL/F); and apparent volume of distribution ($V_d$/F). The PK parameters for solriamfetol in urine included the amount of unchanged drug excreted in urine ($A_e$) over 48 or 72 hours; the fraction of the dose excreted unchanged in urine ($F_e$); and renal clearance of the drug ($CL_R$). For participants on hemodialysis (Group 5), the additional PK parameters included the amount of solriamfetol cleared by the 4-hour hemodialysis ($A_{dial}$); the fraction of dose removed by the 4-hour hemodialysis ($F_{dial}$); and hemodialysis clearance ($CL_{dial}$) calculated as $CL_{dial} = A_{dial} / AUC_{dial}$ where $AUC_{dial}$ is the area under the pre-dialyzer plasma concentration-time curve during the hemodialysis period.

PK parameters were summarized by group using descriptive statistics. To assess differences in PK between each level of renal impairment (Groups 2-5) versus participants with normal renal function (Group 1), a linear effects model was used to compare natural log-transformed PK parameters ($C_{max}$, $AUC_t$, and $AUC_\infty$). For Group 5, the participants without dialysis on day 8 (Group 5.1) and the participants who received dialysis on day 1 (Group 5.2) were analyzed and compared separately.

Point estimates and 90% confidence intervals (CIs) for differences on the natural log scale were exponentiated to obtain estimates for ratios of geometric means on the original scale. The 90% CIs around the geometric means ratios were presented for each pairwise comparison and expressed as a percentage relative to the geometric means of the reference group (Group 1). The inter-participant CV was estimated. To evaluate effects of dialysis on PK parameters for Group 5, an analysis of variance model was used that included "Day" as a fixed effect and measurements within the participant as a repeated measure. Day 8 was used as the reference for comparison. In addition, nonparametric analysis was conducted for $t_{max}$ as appropriate.

All statistical analyses were conducted using SAS version 9.3 (SAS Institute, Cary, NC).

Results

Of the 31 participants who were enrolled and received treatment (6 participants in each of Groups 1 through 4 and 7 participants in Group 5), 30 participants (97%) completed the study. One participant from Group 5 discontinued due to adverse events. Participant demographics (Table 1) show that most participants in Groups 1-4 were white; however, most participants in Group 5 were black. There were at least 2 participants per sex in each group, and mean age for Groups 1, 2, 3, and 4 were comparable with an overlap in the range; the age range in Group 5 was lower than in the other groups. Mean BMI for Groups 1, 2, 3, 4, and 5 were comparable, with an overlap in the range. Furthermore, all participants in Group 1 matched the mean age (±10 years) and BMI (±20%) of participants in Groups 2-5.

TABLE 1

Demographic Characteristics of the Study Population

| Variable | Group 1 Normal renal function (n = 6) | Group 2 Mild renal impairment (n = 6) | Group 3 Moderate renal impairment (n = 6) | Group 4 Severe renal impairment (n = 6) | Group 5 End-stage renal disease (n = 7) |
|---|---|---|---|---|---|
| Sex, n (%) | | | | | |
| Female | 3 (50) | 4 (67) | 2 (33) | 2 (33) | 2 (29) |
| Male | 3 (50) | 2 (33) | 4 (67) | 4 (67) | 5 (71) |
| Race, n (%) | | | | | |
| White | 5 (83) | 5 (83) | 4 (67) | 5 (83) | 1 (14) |
| Black | 1 (17) | 1 (17) | 2 (33) | 1 (17) | 6 (86) |
| Ethnicity, n (%) | | | | | |
| Non-Hispanic or Latino | 0 | 3 (50) | 2 (33) | 3 (50) | 6 (86) |
| Hispanic or Latino | 6 (100) | 3 (50) | 4 (67) | 3 (50) | 1 (14) |
| Age, mean (SD), y | 55.8 (3.9) | 67.8 (7.4) | 70.2 (7.7) | 59.7 (15.6) | 42.0 (7.6) |
| Weight, mean (SD), kg | 73.1 (6.8) | 67.1 (14.2) | 76.8 (11.5) | 85.5 (16.4) | 88.2 (10.5) |
| BMI, mean (SD), kg/m2 | 28.1 (2.7) | 25.1 (4.1) | 28.8 (1.9) | 29.3 (3.0) | 29.9 (3.0) |
| eGFR, mean (SD), mL/min/1.73 m2 | 111.8 (32.3) | 78.5 (8.4) | 44.2 (6.2) | 16.2 (5.8) | 7.4 (4.8) |

BMI = body mass index

Figure 1B:
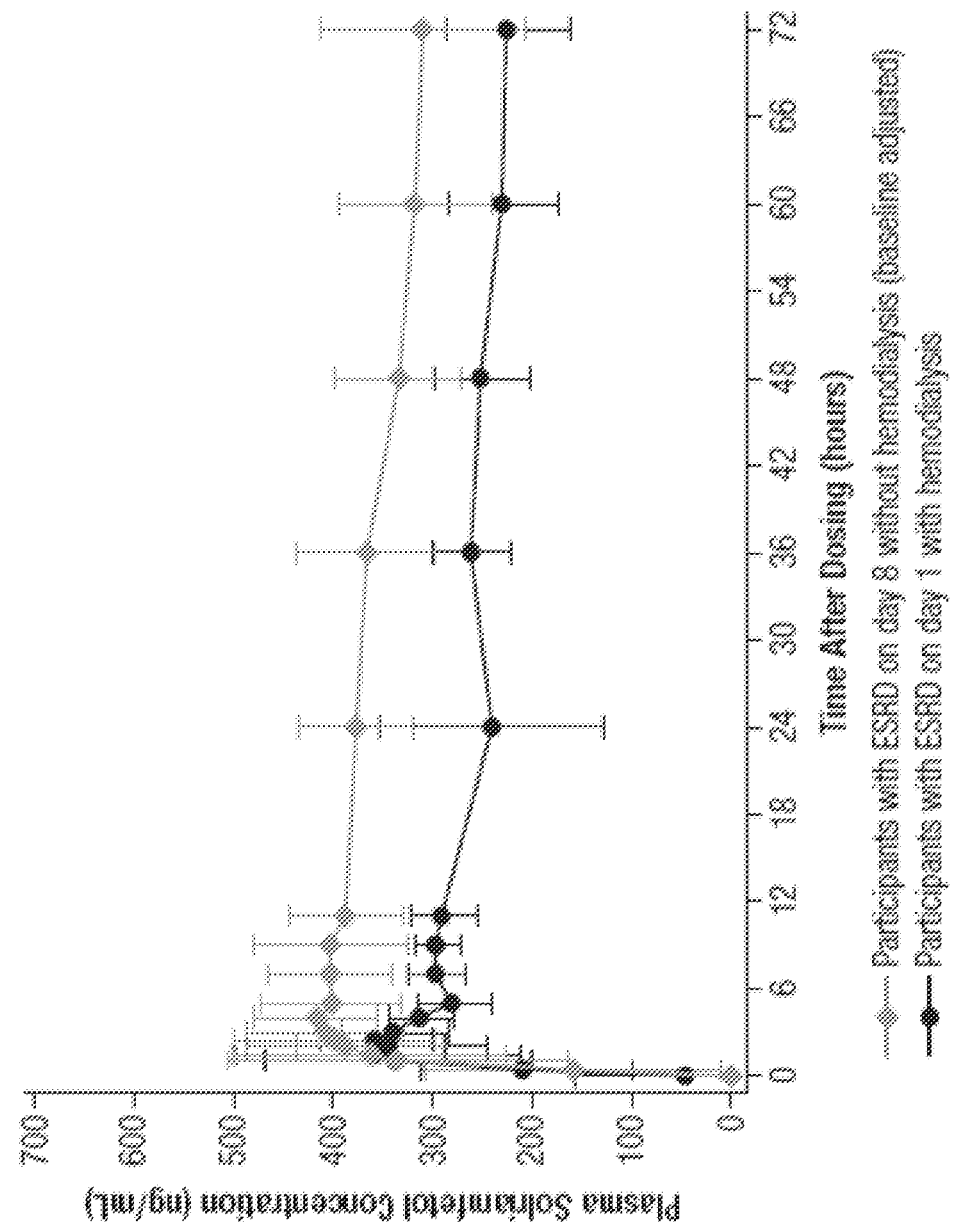
FIG. 1B shows the mean (SD) plasma APC-HCl concentration-time profiles following a single dose equivalent to 75-mg APC for participants with end-stage renal disease with and without hemodialysis.

For all study groups, mean PK parameters are summarized in Table 2 and mean plasma solriamfetol concentration-time profiles are shown in FIGS. 1A and 1B.

TABLE 2

Solriamfetol Pharmacokinetic Parameters by Level of Renal Function

| | Mean ± standard deviation (% coefficient of variation) | | | | | |
|---|---|---|---|---|---|---|
| | Normal renal function | Renal impairment | | | End-stage renal disease (Group 5) | |
| | | | | | Group 5.1 | Group 5.2 |
| Variable | Group 1 (n = 6) | Group 2 Mild (n = 6) | Group 3 Moderate (n = 6) | Group 4 Severe (n = 6) | Without hemodialysis[a] (n = 6) | With hemodialysis (n = 7)[b] |
| $C_{max}$, ng/ml | 499.0 ± 142.4 (28.5) | 521.8 ± 118.8 (22.8) | 517.3 ± 131.6 (25.4) | 552.8 ± 154.4 (27.9) | 474.1 ± 79.0 (16.7) | 396.4 ± 75.4 (19.0) |
| $t_{max}$,[c] h | 1.3 (0.5, 2.0) | 1.5 (0.5, 2.0) | 1.5 (1.0, 2.5) | 2.0 (0.5, 3.0) | 3.3 (1.0, 24.0) | 1.5 (1.5, 10.0) |
| $t_{1/2}$, h | 7.6 ± 5.1 (67.7) | 9.1 ± 1.6 (18.1) | 14.3 ± 4.5 (31.4) | 29.6 ± 14.4 (48.7) | 100.5 ± 78.8 (78.4)[d] | 164.7 ± 81.4 (49.4)[e] |
| $AUC_t$, ng · h/mL[f] | 4849 ± 3454 (71.2) | 6613 ± 1574 (23.8) | 9230 ± 2538 (27.5) | 17 500 ± 9267 (52.9) | 25 580 ± 4544 (17.8) | 18 920 ± 3131 (16.5) |
| $AUC_\infty$, ng · h/mL | 5273 ± 4104 (77.8) | 6836 ± 1730 (25.3) | 10 470 ± 3642 (34.8) | 23 650 ± 16 776 (70.9) | 64 560 ± 35 962 (55.7)[d] | 76 770 ± 41 993 (54.7)[e] |
| CL/F, L/h | 19.8 ± 10.1 (50.9) | 11.5 ± 2.5 (22.1) | 7.8 ± 2.4 (30.5) | 4.7 ± 2.8 (59.4) | 1.6 ± 1.1 (72.3)[d] | 1.5 ± 1.3 (91.0)[e] |
| $V_d$/F, L | 163.9 ± 23.8 (14.5) | 147.2 ± 29.1 (19.8) | 152.0 ± 32.6 (21.4) | 157.2 ± 41.2 (26.2) | 153.6 ± 45.6 (29.7)[d] | 231.4 ± 28.5 (12.3)[e] |

[a]Baseline adjusted to remove the impact of the day 1 dose on the day 8 concentration profile.
[b]Excluding 2 concentration values: 1 participant at predose, and 1 participant at 24 hours.
[c]For tmax, median (min, max) is presented.
[d]n = 3.
[e]n = 6.
[f]Over 48 h for normal, mild, and moderate, and over 72 h for severe.

Figure 2:
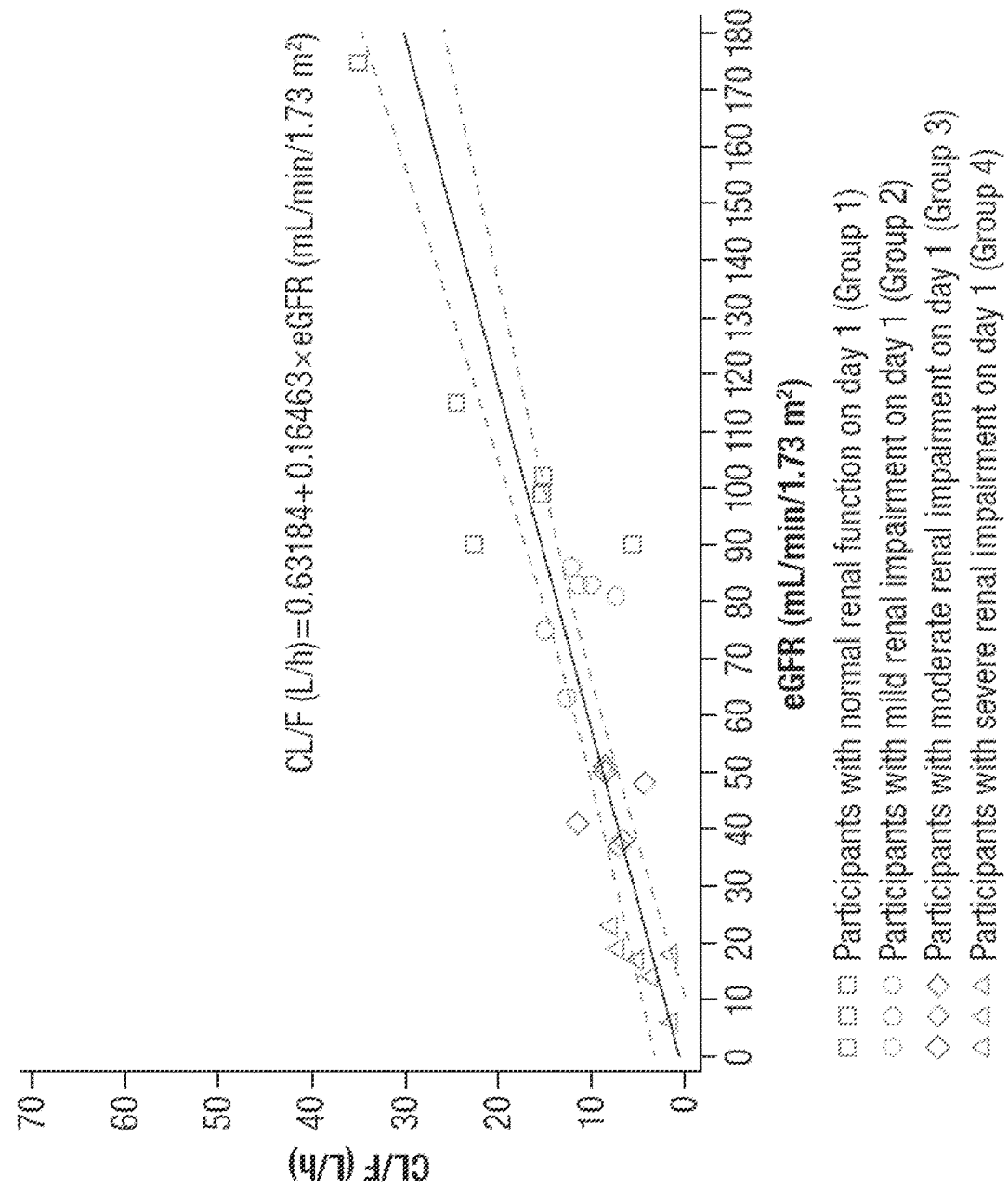
FIG. 2 shows the apparent oral clearance (CL/F) versus day-1 estimated glomerular filtration rate (eGFR) for Groups 1-4. The broken lines represent the 90% confidence intervals.
Figure 3:
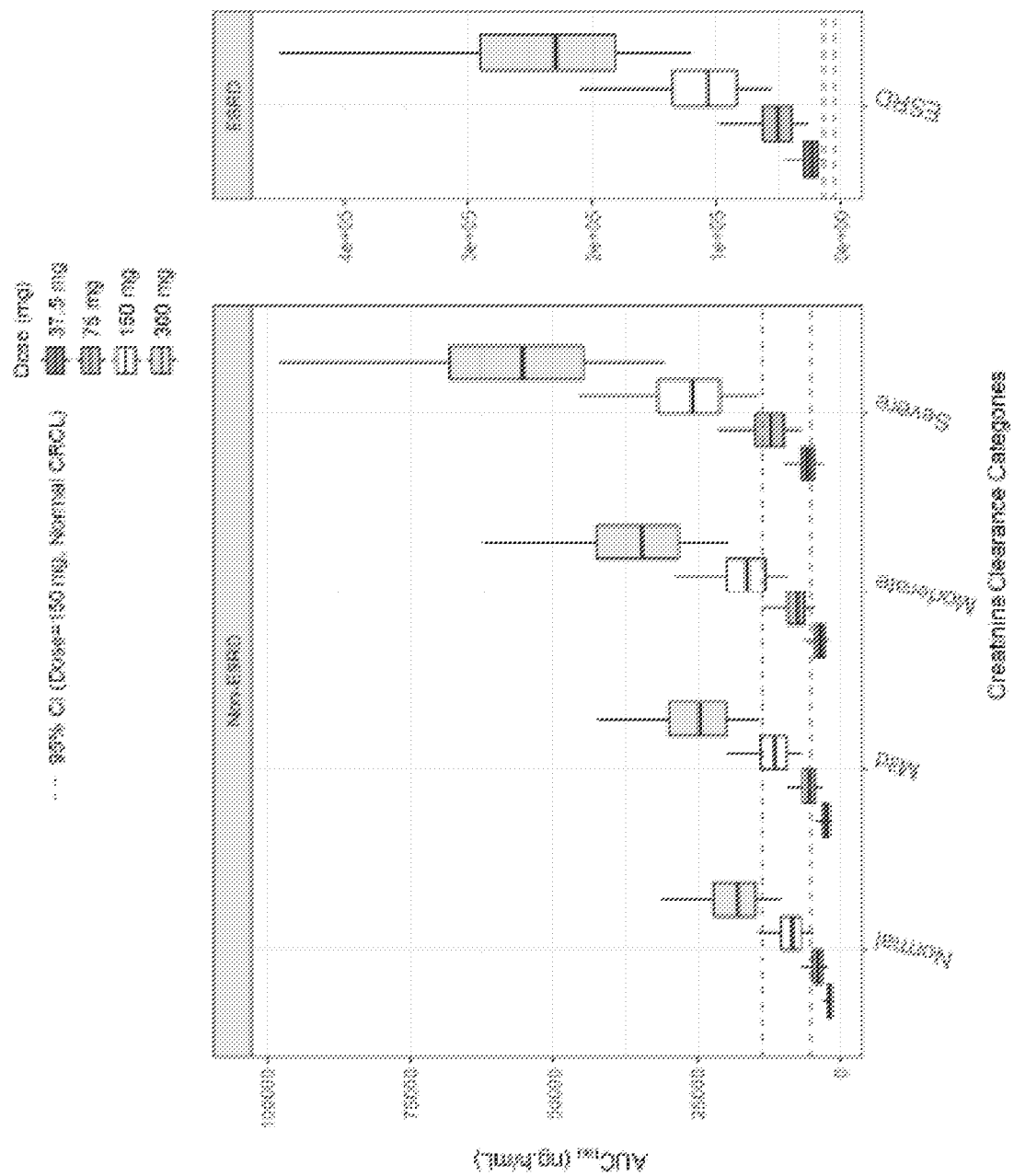
FIG. 3 shows results of simulations to support dosing in sub-populations—comparison of exposure in adult patients (narcolepsy/OSA, tablet, fasting conditions) by renal function—AUCtau.
Figure 4:
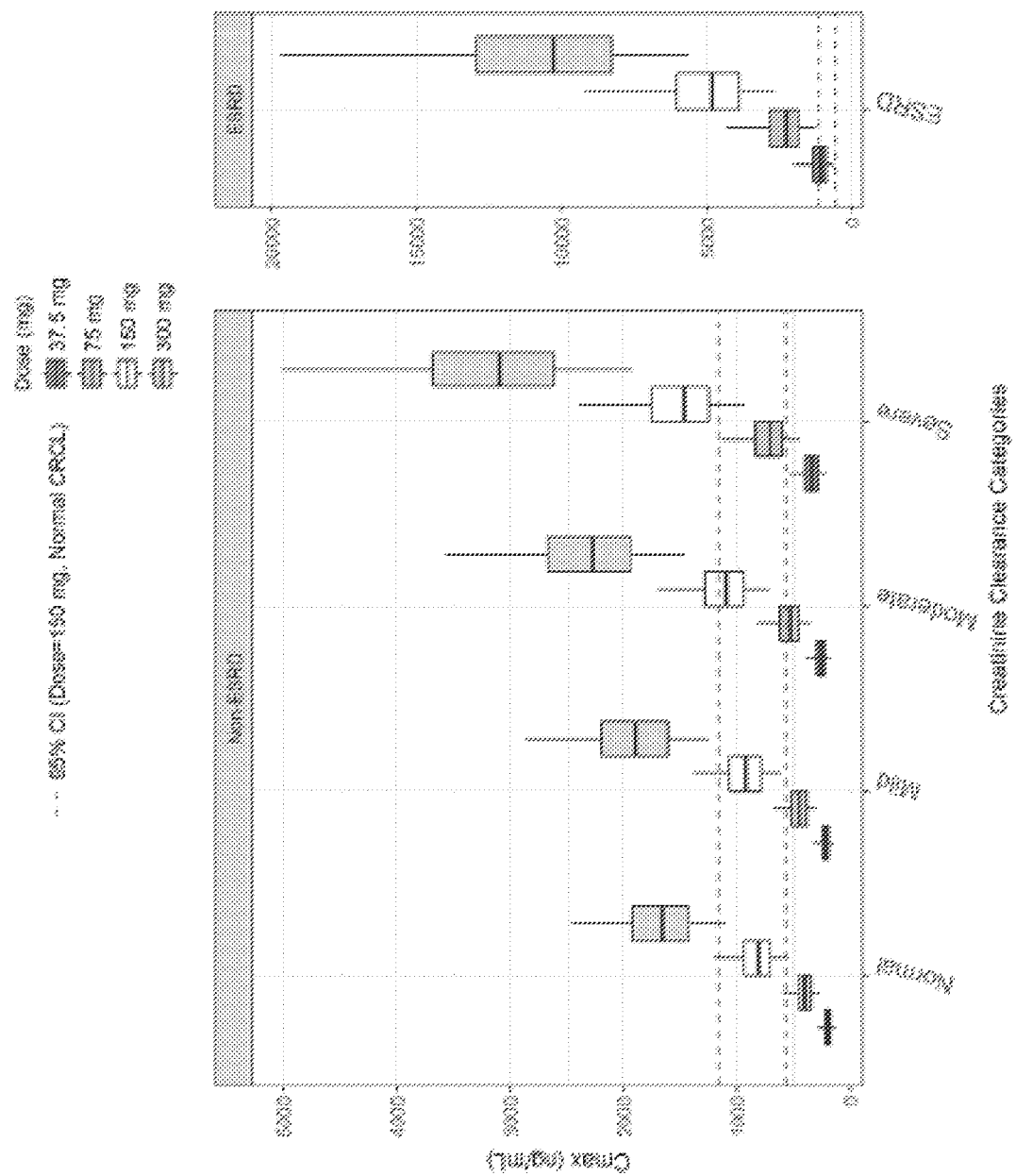
FIG. 4 shows the results of simulations to support dosing in sub-populations—comparison of exposure in adult patients (Narcolepsy/OSA, tablet, fasting conditions) by renal function—Cmax.
Figure 5:
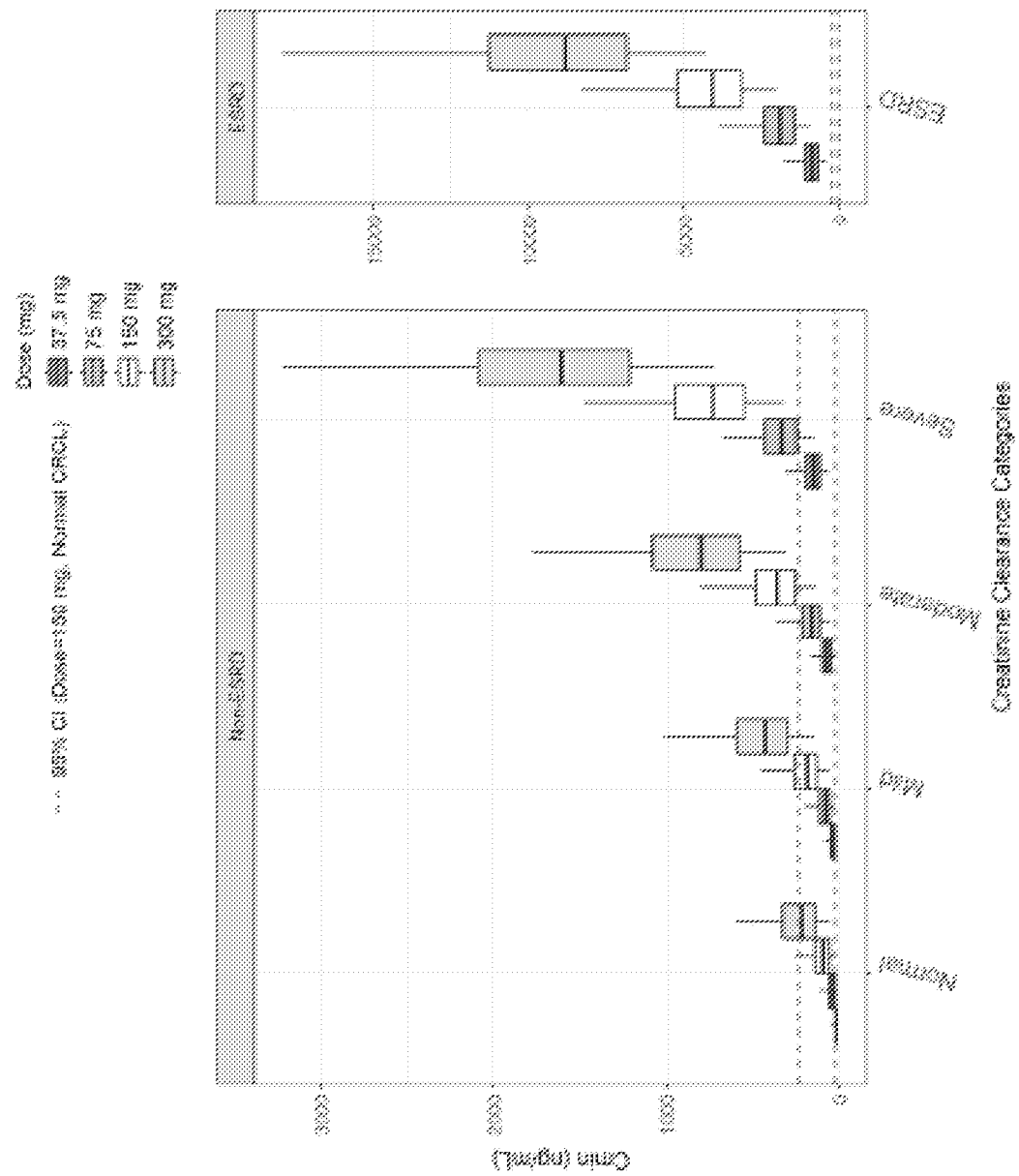
FIG. 5 shows the results of simulations to support dosing in sub-populations—comparison of exposure in adult patients (Narcolepsy/OSA, tablet, fasting conditions) by renal function—Cmin.
Figure 6:
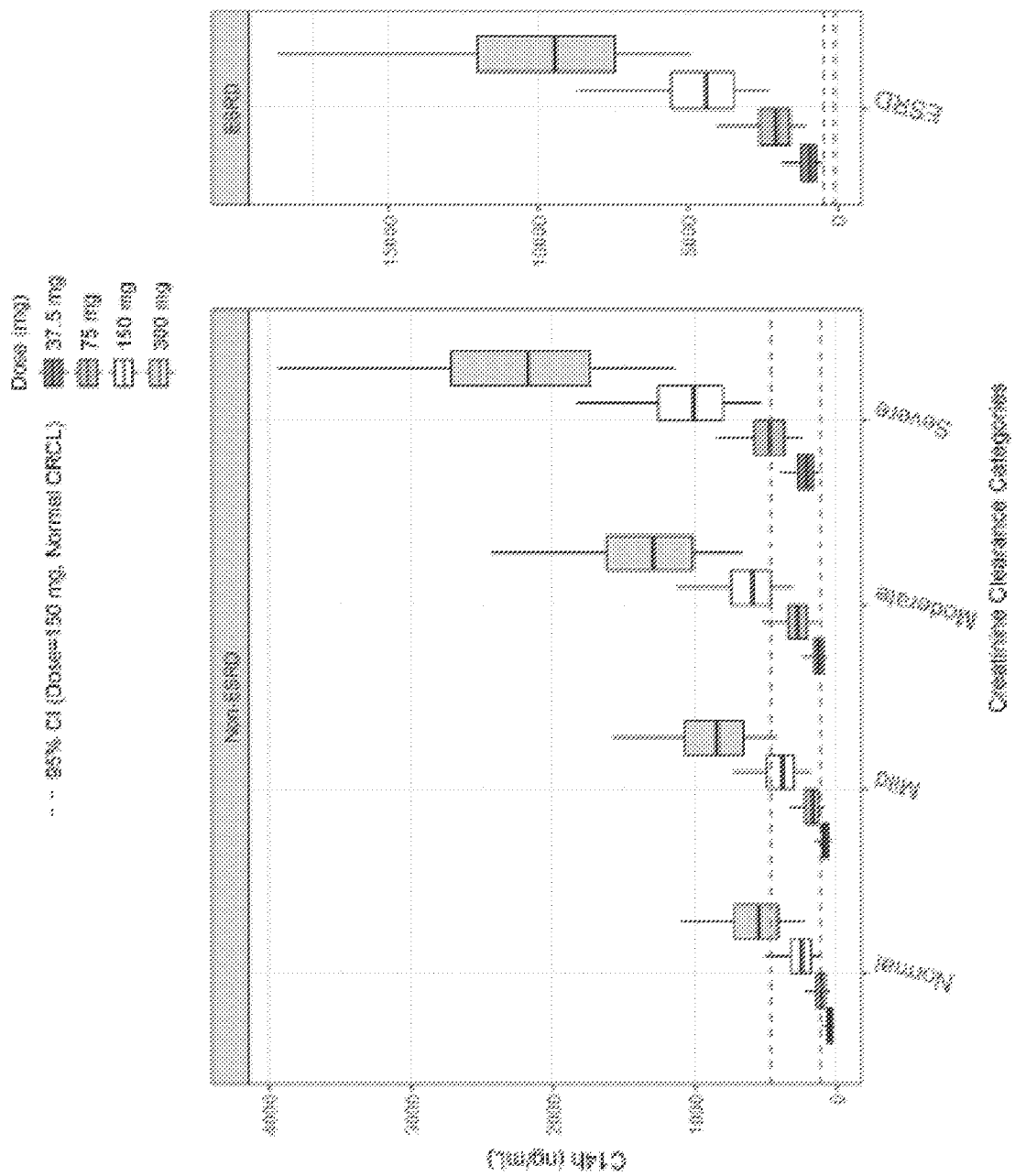
FIG. 6 shows the results of simulations to support dosing in sub-populations—comparison of exposure in adult patients (Narcolepsy/OSA, tablet, fasting conditions) by renal function—C14h.
Figure 7:
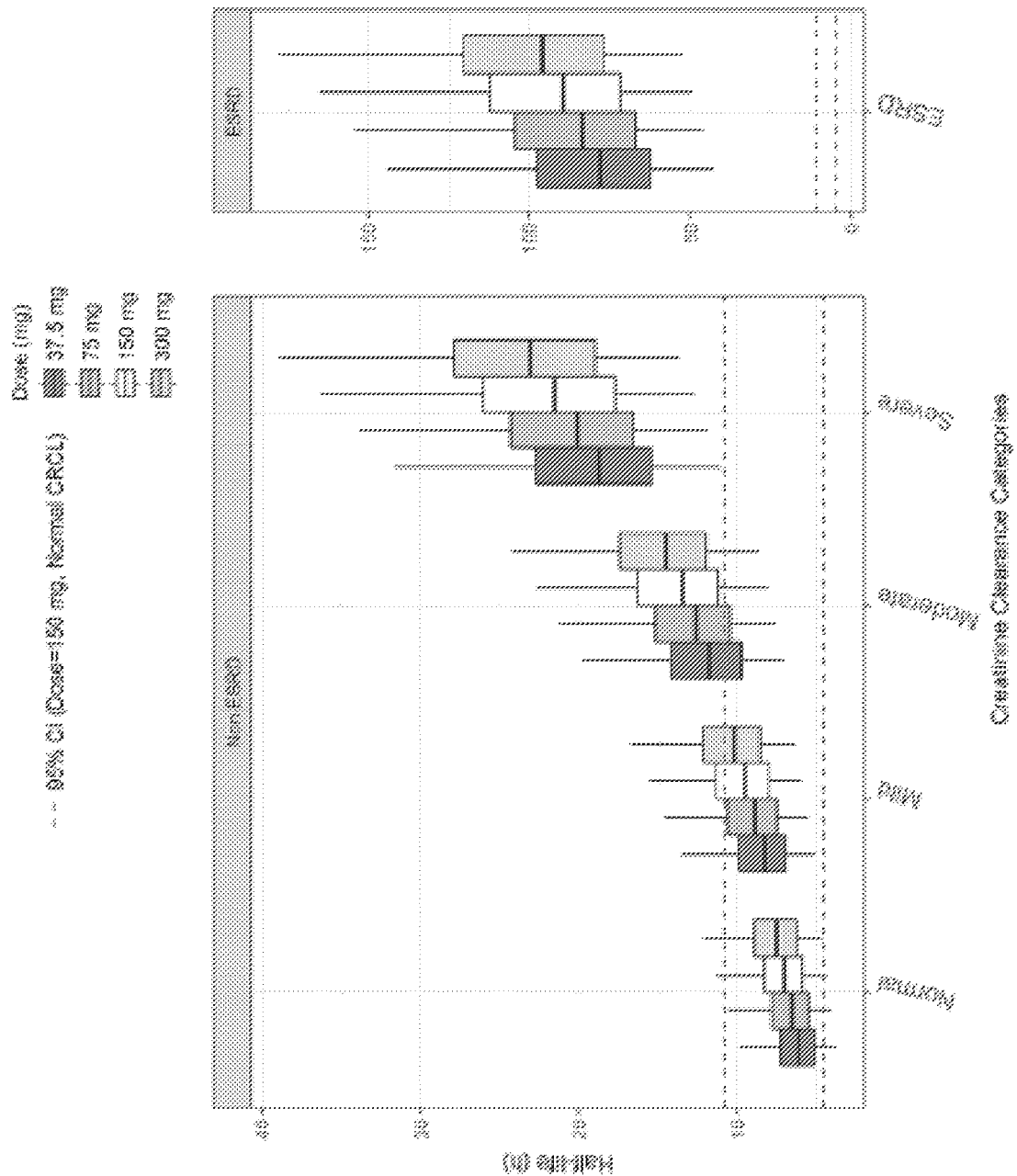
FIG. 7 shows the results of simulations to support dosing in sub-populations—comparison of exposure in adult patients (Narcolepsy/OSA, tablet, fasting conditions) by renal function—half-life.
Figure 8:
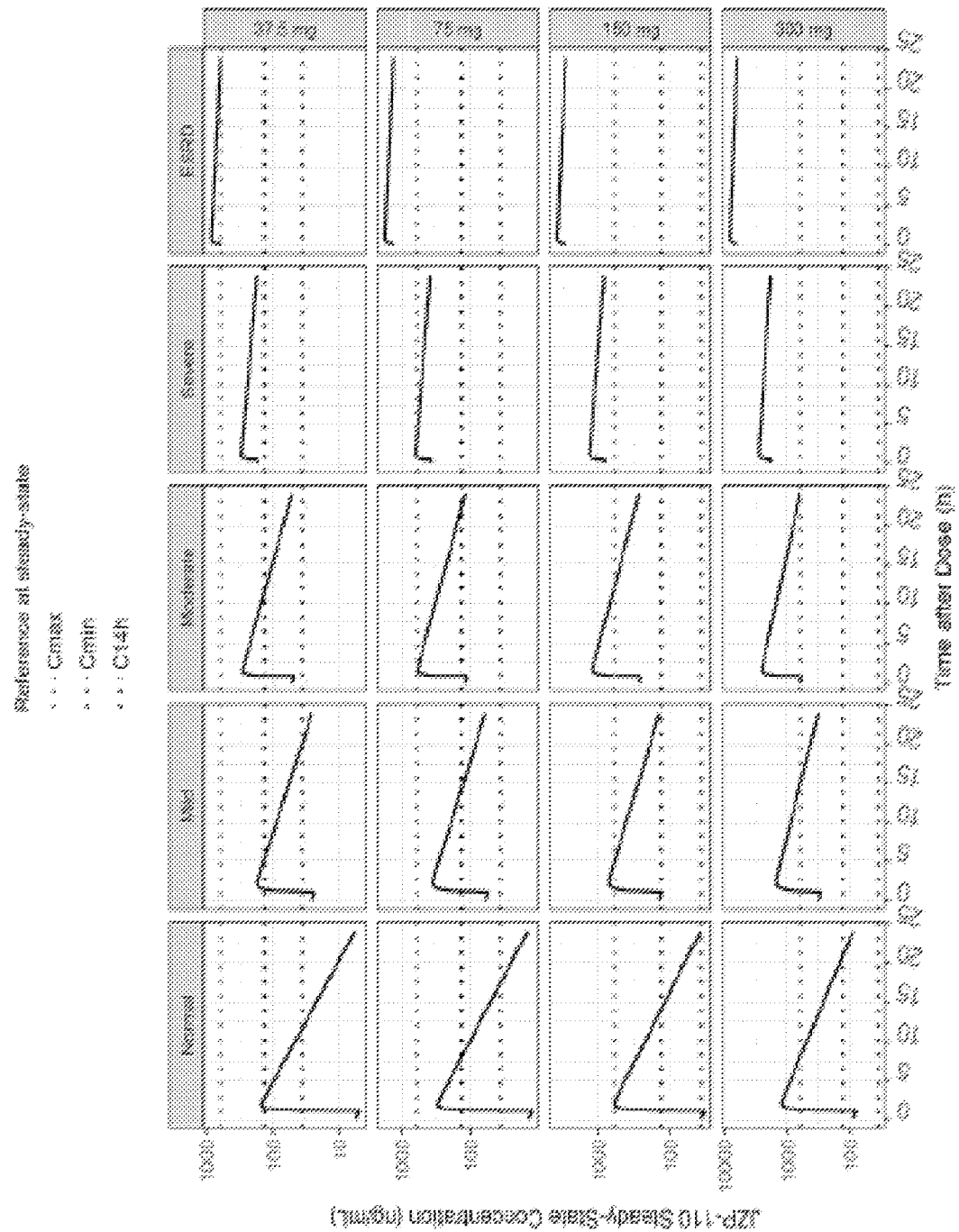
FIG. 8 shows the results of simulations to support dosing in sub-populations—adult patients (Narcolepsy/OSA, tablet, fasting conditions)—individual PK profile (Semi-Log Scale).

In general, mean $C_{max}$ and $t_{max}$ were not substantially affected by renal impairment across Groups 1-4 (Table 2). However, solriamfetol AUC and $t_{1/2}$ values increased with increasing levels of renal impairment. Solriamfetol mean±SD overall exposure (AUC$_\infty$) increased from 5273±4104 ng·h/mL in participants with normal renal function to 6836 ng·h/mL±1730 in Group 2 (mild impairment), 10,470±3642 in Group 3 (moderate impairment), and 23,650±16,776 in Group 4 (severe impairment) (Table 2) Similarly, solriamfetol mean±SD $t_{1/2}$ was 7.6±5.1 hours in participants with normal renal function and increased with greater levels of renal impairment: 9.1±1.6, 14.3±4.5, and 29.6±14.4 hours in Groups 2, 3, and 4, respectively (Table 2). While CL/F decreased with greater levels of renal impairment, there were no substantial changes in $V_d$/F (Table 2). A plot of solriamfetol CL/F versus day −1 eGFR for Groups 1-4 is presented in FIG. 2. This relationship is best described by the equation: solriamfetol CL/F (L/h) =0.63184+0.16463×eGFR (mL/min/1.73 m$^2$).

Among participants with ESRD (Group 5), overall exposure (AUC$_t$) was approximately 5-fold higher for participants without dialysis on day 8 (Group 5.1; 25 580±4544 ng·h/mL) and about 4-fold higher among participants with dialysis on day 1 (Group 5.2; 18 920±3131) relative to Group 1 (4849±3454) (Table 2). Mean $t_{1/2}$ values exceeded 100 hours in both Group 5.1 (100.5 hours) and Group 5.2 (164.7 hours) (Table 2), and compared with Group 1, $C_{max}$ values were slightly lower and $t_{max}$ values differed significantly (P≤0.05 for both).

Ratios of geometric means and their associated 90% CIs for the pairwise comparisons of solriamfetol plasma PK parameters for Groups 2 through 5 versus Group 1 are presented in Table 3.

amfetol exposure (AUC$_\infty$) in Groups 2, 3, and 4 was 53%, 129%, and 339% higher, respectively, relative to Group 1. In participants with ESRD, $C_{max}$ was approximately 3% and 19% lower in groups 5.1 (ESRD without hemodialysis) and 5.2 (ESRD with hemodialysis), respectively, versus Group 1, and exposure was approximately 518% and 357% higher in the 2 groups versus Group 1.

Renal clearance (CL$_R$) and the cumulative amount of solriamfetol excreted in urine decreased as renal impairment increased (Table 4).

TABLE 4

Urinary Excretion of Solriamfetol

| | Mean ± standard deviation (% coefficient of variation) | | | |
|---|---|---|---|---|
| PK parameter | Group 1 Normal renal function (n = 6) | Group 2 Mild (n = 6) | Group 3 Moderate (n = 6) | Group 4 Severe (n = 6) |
| F$_{e(0-48)}$, % | 85.8 ± 7.7 (9.0) | 80.0 ± 9.0 (11.2) | 66.4 ± 12.8 (19.2) | 57.1 ± 18.6 (32.5) |
| CL$_R$, L/h | 17.0 ± 7.7 (45.4) | 9.3 ± 1.6 (17.1) | 5.8 ± 2.0 (34.1) | 3.8 ± 2.6 (68.0) |

CL$_R$, renal clearance; F$_{e(0-48)}$, fraction of the dose excreted unchanged in urine in 48 hours.

In Group 1, the mean±SD percentage of solriamfetol recovered unchanged in urine over 48 hours was 85.8%±7.7% and decreased to 80.0%±9.0%, 66.4%±12.8%, and 57.1%±18.6% in Groups 2, 3, and 4, respectively. Mean solriamfetol renal clearance also decreased with renal impairment, from 17.0±7.7 L/h in the normal renal function

TABLE 3

Comparisons of Solriamfetol Plasma PK Parameters

| PK parameter | Group 1 Normal (n = 6) | Group 2 Mild (n = 6) | Group 3 Moderate (n = 6) | Group 4 Severe (n = 6) | Group 5.1 Without hemodialysis (n = 6) | Group 5.2 With hemodialysis (n = 7)[a] |
|---|---|---|---|---|---|---|
| Geometric LS mean | | | | | | |
| Cmax, ng/ml | 482.3 | 510.5 | 503.2 | 533.0 | 468.8 | 389.9 |
| AUCt, ng·h/mL[b] | 4087.3 | 6469.6 | 8960.2 | 15 549 | 25 253 | 18 689 |
| AUC∞, ng·h/mL | 4363.9 | 6672.4 | 10002 | 19 140 | 56 319[c] | 65 306[d] |
| Percent ratio (90% confidence interval) of geometric mean relative to Group 1 | | | | | | |
| Cmax | — | 105.9 (80.6, 139.0) | 104.3 (78.4, 138.9) | 110.5 (81.1, 150.6) | 97.2 (76.1, 124.1) | 80.9 (63.4,103.1) |
| AUCt | — | 158.3 (97.5, 256.9) | 219.2 (133.7, 359.6) | 380.4 (208.4, 694.4) | 617.8 (385.3, 990.8) | 457.2 (296.6, 704.9) |
| AUC∞ | — | 152.9 (92.9, 251.7) | 229.2 (135.6, 387.4) | 438.6 (217.3, 885.3) | 1290.6 (542.78, 3068.5) | 1496.5 (748.7, 2991.2) |

Notes:
Parameters were ln-transformed prior to analysis. Geometric least-squares means (LSMs) are calculated by exponentiating the LSMs from the analysis of variance. % mean ratio = 100 * (test/reference).
[a]Excluding 2 concentration values: 1 participant at predose, and 1 participant at 24 hours.
[b]Over 48 hours for Groups 1-3 and over 72 hours for Groups 4 and 5.
[c]n = 3.
[d]n = 6.

As shown, small increases were observed in $C_{max}$, which was approximately 6%, 4%, and 11% higher in Groups 2, 3, and 4, respectively, versus Group 1. However, total solrigroup to 9.3±1.6 L/h in Group 2, 5.8±2.0 L/h in Group 3, and 3.8±2.6 L/h in Group 4. Only 1 participant made urine and was able to provide data in Group 5, and the cumulative amount of solriamfetol excreted in urine was lower with hemodialysis, 42.1%, compared with 52.9% without hemodialysis.

Over the 4-hour hemodialysis period on day 1 for participants with ESRD, the mean±SD cumulative fraction of the 75-mg solriamfetol dose removed was 20.6%±1.7% (range 19.2% to 24.1%), and the hemodialysis clearance was 12.4 L/h±1.5 L/h (range 11.3 to 15.9 L/h).

There were no deaths or other serious AEs during this study. A total of 4 participants (13%), 1 each in Groups 2 and 3, and 2 in Group 5 (1 with and 1 without hemodialysis), reported 5 treatment-emergent adverse events (TEAEs; Table 5). This includes single events of nausea, skin abrasion, and headache in 1 participant each, and an increase in alanine aminotransferase (ALT; to 144 IU/L; reference range 8-54 IU/L) and aspartate aminotransferase (AST; to 66 IU/L; reference range 8-40 IU/L) observed 6 days after dosing in 1 participant that led to discontinuation. All TEAEs were considered by the investigator to be mild, and all but the skin abrasion were considered to be related to study drug. All TEAEs resolved, including the increased ALT and AST, which resolved on day 11. No other abnormal laboratory findings were considered clinically meaningful. No clinically significant abnormal findings were observed in vital sign and ECG measurements.

and severe renal impairment, respectively, compared with participants with normal renal function. In this regard, it should also be noted that while $C_{max}$ values were not substantially affected by renal impairment, the observed increases in $t_{1/2}$ associated with renal impairment are expected to translate to changes in steady-state $C_{max}$ that are not fully accounted for by the single-dose regimen evaluated in this clinical study, due to accumulation. AUC and $t_{1/2}$ values increased with increasing levels of renal impairment. Solriamfetol $AUC_{0-inf}$ was higher by approximately 53% (1.53-fold), 129% (2.29-fold), and 339% (4.39-fold) compared with subjects with normal renal function.

Consistent with the inability of ESRD participants requiring hemodialysis to eliminate solriamfetol via renal excretion, these participants had increased overall exposure to solriamfetol (≥4-fold), longer $t_{1/2}$ values (≥13-fold), and slightly lower $C_{max}$ values (≤19%), relative to participants with normal renal function. Furthermore, ESRD participants had lower solriamfetol $C_{max}$ and $AUG_t$ values after undergoing a 4-hour hemodialysis session, with 20.6% of the solriamfetol dose removed as unchanged drug. Notably, the solriamfetol hemodialysis clearance of 12.4 L/h estimated from solriamfetol recovered in the dialysate was approximately 30% lower than solriamfetol renal clearance in participants with normal renal function.

TABLE 5

Number (%) of Participants with Treatment-Emergent Adverse Events (TEAEs)

| Adverse event | Normal renal function | Renal impairment | | | End-stage renal disease (Group 5) | |
|---|---|---|---|---|---|---|
| | Group 1 Normal (n = 6) | Group 2 Mild (n = 6) | Group 3 Moderate (n = 6) | Group 4 Severe (n = 6) | Group 5.1 Without hemodialysis (n = 6) | Group 5.2 With hemodialysis (n = 7) |
| Any TEAE | 0 | 1 (17%) | 1 (17%) | 0 | 1 (17%) | 1 (14%) |
| Nausea | 0 | 0 | 0 | 0 | 1 (17%) | 0 |
| Skin abrasion | 0 | 1 (17%) | 0 | 0 | 0 | 0 |
| ALT increased | 0 | 0 | 0 | 0 | 0 | 1 (14%) |
| AST increased | 0 | 0 | 0 | 0 | 0 | 1 (14%) |
| Headache | 0 | 0 | 1 (17%) | 0 | 0 | 0 |

*One participant from Group 5 discontinued the study before day 8 due to adverse events of mild elevated ALT and AST.
ALT, alanine aminotransferase; AST, aspartate aminotransferase; TEAE, treatment-emergent adverse event.

This study showed that renal impairment increases overall exposure to solriamfetol, with the magnitude of the increase reflecting the level of impairment. The incremental decreases in CL/F with worsening renal function resulted in corresponding increases in overall solriamfetol exposure that was 53% for mild, 129% for moderate, and 339% for severe impairment relative to normal renal function. Increasing renal impairment was also associated with decreasing cumulative percent of solriamfetol excreted in urine. The mean percentage of solriamfetol dose recovered in urine as unchanged drug over 48 hours was 85.8%, 80.0%, 66.4% and 64.0% (over 72 hours) for subjects with normal renal function and for subjects with mild, moderate, and severe renal impairment, respectively. Additionally, since there were no substantial changes in $V_d/F$, the decreases in solriamfetol CL/F resulted in increased $t_{1/2}$ by approximately 1.2-, 1.9-, and 3.9-fold in participants with mild, moderate, Example 2: Simulations of Solriamfetol Exposure in Patients with Renal Impairment Methods A population PK model was developed based on data collected in clinical studies. The population PK model provides a unified characterization of solriamfetol and of its sources of variability across studies and sub-populations of subjects. The population PK analysis examined the influence of potential covariates that have not been evaluated in clinical trials, such as potential differences between narcolepsy and OSA patients, as well as healthy subjects and narcolepsy/OSA patients, and investigated other factors such as age, gender, body weight, race/ethnicity, and formulation effects.

The following thorough evaluation of the source data was performed: (1) Visual inspection of individual plasma concentration-time profiles of solriamfetol relative to actual dosing history (e.g., spaghetti plots for rich concentration-time profiles, mean profiles); (2) Evaluation of potential outliers based on preliminary population PK runs (e.g., using a one compartment model without covariate); and (3) Review of demographic data and baseline characteristics for each study.

The dataset included actual time of observation (sampling and dosing) and main demographic characteristics (covariates) such as age, weight, height, body mass index (BMI), gender, race and markers of renal and liver functions. Extrinsic covariates were also included. The following main variables were included in the analysis dataset.

NMID (unique individual identifier)
STUDY (study identifier)
SUBJ (subject ID used in the study)
DATE (date of the event MM/DD/YYYY)
TIME (time of the event HH:MM)
DV (plasma concentration of solriamfetol, ng/mL)
AMT (actual dose of solriamfetol in mg, calculated based on free base weight)
EVID (event identification for PK observations only: 0=non-below the limit of quantification [BLQ] PK observation, 1=dose administration, 2=other-type event [BLQ PK records])
MDV (missing data code: 0=non-missing, 1=missing data or excluded data)
BLQ (1=BLQ concentration, 0=non-BLQ concentration or dosing event)
FAST (fasted status during administration: 1=fasted; 0=fed)
FORM (formulation: 0=drug substance in capsule; 1=tablet; 2=over-encapsulated tablet)
Daily dose (actual dose of solriamfetol in mg, calculated based on free base weight)
DS (disease status: 0=healthy subjects, 1=subjects with narcolepsy; 2=subjects with OSA)
WT (body weight at screening in kg)
Age at baseline (age in years)
Age as a categorical covariate (i.e., non-elderly vs. elderly ≥65 years old)
Race (White, Black, Asian, Native Hawaiian or other Pacific Islander, Hispanic, Oriental, other)
Ethnicity (1=Hispanic or Latino, 0=non-Hispanic or Latino)
Gender (0=female, 1=male)
TAD (time after previous dose in h)
VISIT (visit number)
NTIME (nominal time after the dose in hours)
CRCL at baseline (creatinine clearance in mL/min calculated by Cockcroft-Gault formula) (Cockcroft D W, Gault M H: Prediction of creatinine clearance from serum creatinine. Nephron 1976; 16: 31-41)
eGFR at baseline
Renal impairment status based on Food and Drug Administration (FDA) guidance10:
  Normal: eGFR≥90 mL/min/1.73 m$^2$
  Mild: eGFR 60-89 mL/min/1.73 m$^2$ (i.e., ≥60 to <90)
  Moderate: eGFR 30-59 mL/min/1.73 m$^2$ (i.e., ≥30 to <60)
  Severe: eGFR 15-29 mL/min/1.73 m$^2$ (i.e., ≥15 to <30) and not on hemodialysis
  End-stage renal disease (ESRD): eGFR<15 mL/min/1.73 m$^2$ and not on hemodialysis or patients on hemodialysis
HT (height in m)
BMI at baseline (body mass index in kg/m$^2$)
BSA at baseline (body surface area, calculated by Dubois and Dubois formula) (DuBois D; DuBois E F: A formula to estimate the approximate surface area if height and weight be known. Arch Int Med 1916 17:863-71)
ALT at baseline (alanine aminotransferase in U/L)
AST at baseline (aspartate aminotransferase in U/L)
ALB at baseline (albumin in g/L)
Bioanalytical method (High performance liquid chromatography [HPLC] or Liquid chromatography-tandem mass spectrometry [LC-MS/MS]).

Base Population PK Model Buildup

In a first step, compartmental PK models without covariates were evaluated to assess the PK of solriamfetol. One and two-compartment models with linear disposition were tested to assess the concentration-time profiles of solriamfetol.

Model Buildup

The population PK model included the following.

1. A structural component describing the relationships between plasma concentration and time using the following equation:

$$Cp_{ij}=C(D_i,t_j,\theta_i)\cdot(1+\varepsilon_{p,ij})+\varepsilon_{a,ij}$$

$$\theta_i=(\theta_{i1},\ldots,\theta_{ip})$$

wherein $Cp_{ij}$ is the concentration at the $j^{th}$ collection time $t_j$ for subject i, Di represents dosing history for subject i, $\vartheta_i$ is the vector of p different PK parameters for subject i, and $\varepsilon_{p,ij}$ and $\varepsilon_{a,ij}$ are the proportional and additive random residual error terms, respectively, associated with jth concentration for subject i. $\varepsilon_p$ and $\varepsilon_a$ are normally distributed with mean 0 and variances $\sigma_p 2$ and $\sigma_a^2$, respectively.

2. A variance component characterizing between-subject variability (BSV) and, if required, inter-occasion variability (IOV) in model parameters.

$$\theta_{ink}=(\theta_{TV,n}e^{(\eta_{in}+\psi_{ink})})$$

$$(\eta_1,\ldots,\eta_p)=MVN(0,\Omega)$$

$$\psi_{nk}=N(0,\Phi_n)$$

where $\theta_{ink}$ is the value of the $n^{th}$ PK parameter of the ith individual on the kth occasion, $\theta_{TV,n}$ is the typical value of the nth PK parameter in the population, $\eta_{in}$ is the random inter-individual deviation from the typical value $\theta_{TV,n}$ for subject i, and $\psi_{ink}$ is the random inter-occasion subject deviation from the value of the nth parameter for subject i on occasion k. Inter-individual random effects $(\eta_1,\ldots,\eta_m)$, also known as ETAs, are multivariate normally distributed with mean 0 and estimated variance cone included in the variance-covariance OMEGA ($\Omega$) matrix. Inter-occasion random effects for the nth parameter $\psi_{nk}$ are normally distributed with mean 0 and variance $\Phi_n$, with all $\psi_{n1},\ldots,\psi_{nm}$ sharing the same variance, where m is the number of occasions.

The evaluation of the BSV/IOV models included possible addition of BSV terms (ETAs) to the model parameters, evaluation of the most appropriate form of the ETAs, and evaluation of pair-wise plots of the ETAs for any correlations. Covariance between ETA terms was estimated in the model where correlations between ETAs were deemed probable based on these diagnostic plots. Models with shared ETA were also considered.

3. Error models describing residual unexplained variability in the form of additive, proportional or additive and proportional models:

$$y_{ij} = \hat{y}_{ij} * (1+\varepsilon_{1ij}) + \varepsilon_{2ij}$$

where $y_{ij}$ and $\hat{y}_{ij}$ represent the jth observed and predicted plasma drug concentration for the ith participant and $\varepsilon$ is the random residual variability. Each $\varepsilon$ ($\varepsilon_1$ and $\varepsilon_2$) is normally distributed with mean 0 and variance $\sigma^2$. An allometric function accounting for body weight effect on clearance (CL/F) and volume of distribution (V/F) was included in the model. In addition, the effect of creatinine clearance was added on CL/F since the drug was previously demonstrated to undergo important renal excretion.

Model Evaluation

Consistent with the FDA/EMA Guidance for Industry, evaluation of the models was based on the following.

Standard model diagnostics and standard statistical criteria of goodness-of-fit criteria such as the log-likelihood difference between alternative models (e.g., a decrease in the objective function value [OFV])

Successful model convergence

Examining pertinent graphical representations of goodness-of-fit:
  Observed data versus population predicted data (DV vs. PRED) and individual predicted data (DV vs. IPRED) with a line of unity and a trend line, on linear and log scales
  Observed Data versus time after the 1st dose and after the previous dose (DV vs. time and DV vs. TAD) with trend lines of DV and PRED, on linear and log scales
  Conditional weighted residuals versus predicted data (CWRES vs. PRED) with zero line and a trend line
  Conditional weighted residuals versus time after the 1st dose and previous dose [CWRES vs. time and CWRES vs. TAD] with zero line and a trend line
  Quantile-quantile plot of CWRES (QQ plot)

Estimating shrinkage of the empirical Bayesian estimates (EBEs) of the model parameters was evaluated for diagnostic purpose. The shrinkage magnitude for a structural parameter $\theta$ ($\eta$-shrinkage) was calculated as follow:

$$sh_\theta = 1 - \frac{SD(\eta_{EBE,P})}{\omega_\theta}$$

where $SD(\eta_{EBE,P})$ is the standard deviation of the individual EBEs for parameter P, $\omega_P$ is the model estimate of the standard deviation associated with parameter P. If no shrinkage in parameter P is present, the ratio between $SD(\eta_{EBE,P})$ and $\omega_P$ is unity, and shP becomes zero. Shrinkage reflects the degree of information available in the data to estimate the random effects independently, where a shrinkage of 100% reflects a case where there is no information at all on the random effect and all individual parameters revert back to the population estimate. Covariate effects may be interpreted with caution for PK parameters associated with high shrinkage (e.g., >30%), as the individual random effect estimates are expected to shrink towards zero.

Incorporation of Assay Conversion Factor

All plasma samples were assayed using an LC-MS/MS or an HPLC method. Exploratory analyses were performed to investigate potential differences in concentrations determined using the two different methods, and were used to guide further steps in model development, and whether or not an effect of assay was to be included as part of the base population PK model or the residual error model. As a consequence of the observed differences in concentrations due to use of the two different assay methodologies, an assay conversion factor (CF) was incorporated into the model to scale solriamfetol concentrations from HPLC assay to LC-MS/MS as per the following linear and nonlinear models:

Linear CF: $C_{LC-MS/MS} = (C_{HPLC}) \times CF$

Nonlinear CF: $C_{LC-MS/MS} = (C_{HPLC})^{CF}$

In addition, different error models were considered for each assay. The CF was tested in the additive and proportional components of the error models. The selection of the final CF model was based on quality-of-fit using standard graphical representations of goodness-of-fit, including the diagnostic plots.

Sources of Variability and Covariate Analysis

The relationships between PK parameters and covariates were explored graphically to identify the covariates likely to affect the PK of solriamfetol. Scatter plots of the relationships between the random effect of PK parameters and continuous variables included LOESS lines, Pearson correlation coefficients, and the corresponding p-value for each relationship. Box plots were used to describe the relationship for categorical covariates. The investigated intrinsic factors included the following.

Age at baseline (as a continuous covariate in years and/or categorical covariate [i.e., non-elderly (18-64) vs. elderly (?65 years old)]). Covariate was tested on CL/F, V/F and Ka.

Gender. Covariate was tested on CL/F and V/F.

Measures of body size at baseline (i.e., body weight): Included in the base model on CL/F and V/F.

Ethnic origin/Race. Covariates were tested on CL/F and V/F.

Markers of renal function at baseline (based on creatinine clearance): Included in the base model on CL/F.

Markers of liver function at baseline (ALB, ALT and AST). Covariates were tested on CL/F and V/F.

The investigated extrinsic factors included:

Nominal dose levels of JZP-110. Covariate was tested on CL/F, V/F and Ka.

Formulation (Over-encapsulated Tablet vs. Tablet vs. drug substance in Capsule). Covariate was tested on CL/F, V/F and Ka.

Fasted status (i.e., fed vs. fasted). Covariate was tested on Tlag and Ka.

Disease status. Covariate was tested on CL/F and V/F.
  Healthy subjects
  Subjects with narcolepsy
  Subjects with OSA In the next step, the most relevant covariates were formally evaluated within the population PK model using a stepwise forward additive approach using a p-value of 0.01 ($\Delta OFV=6.63$, for one degree of freedom [df]) and a backward elimination approach using a p-value of 0.001 ($\Delta OFV=10.83$, for one df).

In addition, a nonparametric bootstrap resampling analysis was performed. The bootstrap technique involves repeatedly drawing random samples from the original data, with replacement. The bootstrap was used to reduce the model by removing covariates for which the 95% prediction interval (PI) included the null value relative to the reference population. Statistically significant covariates identified during the covariate analysis were displayed graphically in a forest plot. See, Menon-Andersen D, Yu B, Madabushi R, Bhattaram V, Hao W, Uppoor R S, Mehta M, Lesko L, Temple R, Stockbridge N, Laughren T, Gobburu J V. Essential pharmacokinetic information for drug dosage decisions: a concise visual presentation in the drug label. Clin Pharmacol Ther. 2011 September; 90(3):471-4.

Final Model

The final population PK model was evaluated using visual predictive check (VPC). Based on the estimates of the final model, concentration-time profiles were simulated using 1000 replicates. Observed and simulated data were separated into distinct bins. Within each bin, a 95% confidence interval of the 5th, $50^{th}$ and 95th prediction intervals was obtained by simulation. The confidence intervals give an indication of the uncertainty of the predictions. The 5th, 50th and 95th percentiles of observed concentrations were compared to the 95% confidence intervals.

The final population PK model was used to simulate rich concentration-time profiles of solriamfetol in adult subjects with renal impairment (mild, moderate, severe, and ESRD) and in pediatric patients following administration of different dosing regimens.

The final population PK model was used to perform simulations in 10000 narcolepsy/OSA patients for each dose level of solriamfetol tablet formulation (37.5, 75, 150, and 300 mg), and exposure parameters (AUCtau, Cmax, Cmin, C14h and t1/2) were derived.

Descriptive statistics of exposure parameters for each dose level and according to each renal impairment category are presented in Tables 6-10. Boxplots of exposure parameters for each dose level and according to each renal impairment category are presented in FIGS. 3-7. Simulated concentration-time profiles for each dose level and according to each renal impairment category are presented in Table 8.

TABLE 6

Simulations to Support Dosing in Sub-Populations - Adult Patients (Narcolepsy/OSA, tablet, fasting conditions) with Normal Renal Function

| | Dose (mg) - Solriamfetol | | | |
|---|---|---|---|---|
| Parameters | 37.5 (n = 10000) | 75 (n = 10000) | 150 (n = 10000) | 300 (n = 10000) |
| $AUC_{tau}$ (ng · h/mL) | | | | |
| Mean (CV %) | 1931 (34.4%) | 4139 (34.4%) | 8874 (34.4%) | 19024 (34.4%) |
| Median | 1822 | 3906 | 8382 | 17952 |
| [Min, Max] | [471, 7671] | [1010, 16473] | [2165, 35375] | [4641, 75968] |
| Geom. Mean (Geom. CV %) | 1825 (34.6%) | 3912 (34.6%) | 8387 (34.6%) | 17980 (34.6%) |
| $C_{max}$ (ng/mL) | | | | |
| Mean (CV %) | 202 (24.5%) | 410 (24.6%) | 835 (24.8%) | 1702 (25.0%) |
| Median | 197 | 399 | 811 | 1654 |
| [Min, Max] | [79.1, 494] | [160, 1004] | [323, 2086] | [656, 4370] |
| Geom. Mean (Geom. CV %) | 196 (24.5%) | 398 (24.6%) | 810 (24.8%) | 1651 (25.0%) |
| $C_{min}$ (ng/mL) | | | | |
| Mean (CV %) | 19.6 (78.9%) | 46.7 (75.0%) | 110 (71.5%) | 259 (68.4%) |
| Median | 15.8 | 38.3 | 92.2 | 219 |
| [Min, Max] | [0.0290, 194] | [0.104, 432] | [0.362, 961] | [1.21, 2132] |
| Geom. Mean (Geom. CV %) | 14.3 (108%) | 35.0 (99.2%) | 84.9 (92.1%) | 204 (85.9%) |
| $C_{14\,h}$ (ng/mL) | | | | |
| Mean (CV %) | 53.6 (50.3%) | 120 (48.5%) | 268 (46.9%) | 595 (45.5%) |
| Median | 49.1 | 111 | 248 | 552 |
| [Min, Max] | [1.21, 296] | [3.39, 642] | [9.32, 1390] | [25.1, 3007] |
| Geom. Mean (Geom. CV %) | 47.1 (57.7%) | 106 (54.7%) | 240 (52.2%) | 536 (50.0%) |
| Half-life (h) | | | | |
| Mean (CV %) | 6.35 (30.7%) | 6.81 (30.7%) | 7.30 (30.7%) | 7.82 (30.7%) |
| Median | 6.08 | 6.52 | 6.99 | 7.50 |
| [Min, Max] | [1.71, 21.4] | [1.83, 22.9] | [1.96, 24.5] | [2.10, 26.3] |
| Geom. Mean (Geom. CV %) | 6.08 (30.5%) | 6.51 (30.4%) | 6.98 (30.4%) | 7.48 (30.5%) |

$AUC_{tau}$: Area under the concentration-time curve at steady state; $C_{14\,h}$: concentration at 14 h post-dose at steady state; $C_{max}$: maximum concentration at steady state; $C_{min}$: concentration at 24 h post-dose at steady state; CV %: coefficient of variation; Min: minimum; Max: maximum; n: number of subjects.

TABLE 7

Simulations to Support Dosing in Sub-Populations - Adult Patients (Narcolepsy/OSA, tablet, fasting conditions) with Mild Renal Impairment

| Parameters | Reference (Adult, Dose = 150 mg, Normal Renal Function) | Dose | | | |
|---|---|---|---|---|---|
| | | 37.5 mg (n = 10000) | 75 mg (n = 10000) | 150 mg (n = 10000) | 300 mg (n = 10000) |
| $AUC_{tau}$ (ng · h/mL) | | | | | |
| Mean (CV %) | 8874 (34.4%) | 2624 (34.3%) | 5626 (34.2%) | 12059 (34.2%) | 25853 (34.2%) |
| Median | 8382 | 2479 | 5320 | 11395 | 24428 |
| [Min, Max] | [2165, 35375] | [721, 9598] | [1548, 20619] | [3321, 44294] | [7124, 95152] |
| Geom. Mean (Geom. CV %) | 8387 (34.6%) | 2482 (34.4%) | 5321 (34.3%) | 11407 (34.3%) | 24453 (34.3%) |
| $C_{max}$ (ng/mL) | | | | | |
| Mean (CV %) | 835 (24.8%) | 225 (24.8%) | 461 (25.1%) | 946 (25.3%) | 1945 (25.6%) |
| Median | 811 | 219 | 448 | 919 | 1890 |
| [Min, Max] | [323, 2086] | [82.4, 550] | [167, 1158] | [338, 2444] | [686, 5171] |
| Geom. Mean (Geom. CV %) | 810 (24.8%) | 218 (24.8%) | 447 (25.1%) | 917 (25.3%) | 1884 (25.6%) |
| $C_{min}$ (ng/mL) | | | | | |
| Mean (CV %) | 110 (71.5%) | 39.8 (64.5%) | 91.8 (61.9%) | 211 (59.5%) | 482 (57.4%) |
| Median | 92.2 | 34.3 | 80.1 | 186 | 428 |
| [Min, Max] | [0.362, 961] | [0.677, 289] | [2.06, 636] | [6.09, 1396] | [17.5, 3062] |
| Geom. Mean (Geom. CV %) | 84.9 (92.1%) | 32.2 (77.9%) | 75.7 (73.3%) | 177 (69.3%) | 409 (65.8%) |
| $C_{14\,h}$ (ng/mL) | | | | | |
| Mean (CV %) | 268 (46.9%) | 84.9 (43.8%) | 187 (42.6%) | 411 (41.6%) | 902 (40.8%) |
| Median | 248 | 79.1 | 175 | 384 | 845 |
| [Min, Max] | [9.32, 1390] | [8.46, 385] | [21.3, 830] | [52.6, 1791] | [128, 3861] |
| Geom. Mean (Geom. CV %) | 240 (52.2%) | 77.2 (47.2%) | 171 (45.6%) | 378 (44.1%) | 831 (42.9%) |
| Half-life (h) | | | | | |
| Mean (CV %) | 7.30 (30.7%) | 8.67 (30.8%) | 9.29 (30.7%) | 9.96 (30.7%) | 10.7 (30.7%) |
| Median | 6.99 | 8.26 | 8.85 | 9.48 | 10.2 |
| [Min, Max] | [1.96, 24.5] | [2.69, 26.1] | [2.88, 28.0] | [3.09, 30.0] | [3.31, 32.2] |
| Geom. Mean (Geom. CV %) | 6.98 (30.4%) | 8.29 (30.4%) | 8.89 (30.4%) | 9.53 (30.4%) | 10.2 (30.4%) |

$AUC_{tau}$: Area under the concentration-time curve at steady state; $C_{14\,h}$: concentration at 14 h post-dose at steady state; $C_{max}$: maximum concentration at steady state; $C_{min}$: concentration at 24 h post-dose at steady state; CV %: coefficient of variation; Min: minimum; Max: maximum; n: number of subjects.

TABLE 8

Simulations to Support Dosing in Sub-Populations - Adult Patients (Narcolepsy/OSA, tablet, fasting conditions) with Moderate Renal Impairment

| Parameters | Reference (Adult, Dose = 150 mg, Normal Renal Function) | Dose | | | |
|---|---|---|---|---|---|
| | | 37.5 mg (n = 10000) | 75 mg (n = 10000) | 150 mg (n = 10000) | 300 mg (n = 10000) |
| $AUC_{tau}$ (ng · h/mL) | | | | | |
| Mean (CV %) | 8874 (34.4%) | 3743 (36.6%) | 8024 (36.6%) | 17201 (36.5%) | 36875 (36.5%) |
| Median | 8382 | 3518 | 7539 | 16157 | 34617 |
| [Min, Max] | [2165, 35375] | [777, 14484] | [1666, 31285] | [3570, 67577] | [7652, 145970] |
| Geom. Mean (Geom. CV %) | 8387 (34.6%) | 3517 (36.4%) | 7540 (36.4%) | 16164 (36.3%) | 34651 (36.3%) |
| $C_{max}$ (ng/mL) | | | | | |
| Mean (CV %) | 835 (24.8%) | 266 (26.8%) | 550 (27.2%) | 1139 (27.6%) | 2366 (28.0%) |
| Median | 811 | 255 | 527 | 1093 | 2267 |
| [Min, Max] | [323, 2086] | [87.6, 810] | [179, 1712] | [365, 3624] | [748, 7684] |
| Geom. Mean (Geom. CV %) | 810 (24.8%) | 257 (26.4%) | 531 (26.8%) | 1099 (27.2%) | 2280 (27.6%) |
| $C_{min}$ (ng/mL) | | | | | |
| Mean (CV %) | 110 (71.5%) | 78.3 (57.9%) | 177 (56.1%) | 397 (54.5%) | 888 (53.0%) |
| Median | 92.2 | 69.6 | 158 | 356 | 801 |
| [Min, Max] | [0.362, 961] | [1.00, 434] | [2.86, 961] | [7.96, 2126] | [21.7, 4695] |

TABLE 8-continued

Simulations to Support Dosing in Sub-Populations - Adult Patients (Narcolepsy/OSA, tablet, fasting conditions) with Moderate Renal Impairment

| Parameters | Reference (Adult, Dose = 150 mg, Normal Renal Function) | Dose | | | |
|---|---|---|---|---|---|
| | | 37.5 mg (n = 10000) | 75 mg (n = 10000) | 150 mg (n = 10000) | 300 mg (n = 10000) |
| Geom. Mean (Geom. CV %) | 84.9 (92.1%) | 66.4 (65.6%) | 151 (62.8%) | 343 (60.2%) | 774 (58.0%) |
| $C_{14\,h}$ (ng/mL) | | | | | |
| Mean (CV %) | 268 (46.9%) | 135 (42.4%) | 293 (41.7%) | 638 (41.1%) | 1385 (40.5%) |
| Median | 248 | 125 | 273 | 594 | 1294 |
| [Min, Max] | [9.32, 1390] | [9.10, 573] | [22.4, 1243] | [54.3, 2699] | [130, 5855] |
| Geom. Mean (Geom. CV %) | 240 (52.2%) | 123 (44.1%) | 270 (43.1%) | 588 (42.3%) | 1281 (41.5%) |
| Half-life (h) | | | | | |
| Mean (CV %) | 7.30 (30.7%) | 12.4 (32.6%) | 13.2 (32.5%) | 14.2 (32.5%) | 15.2 (32.5%) |
| Median | 6.99 | 11.8 | 12.6 | 13.5 | 14.5 |
| [Min, Max] | [1.96, 24.5] | [3.14, 40.3] | [3.37, 43.2] | [3.61, 46.3] | [3.87, 49.7] |
| Geom. Mean (Geom. CV %) | 6.98 (30.4%) | 11.8 (32.4%) | 12.6 (32.4%) | 13.5 (32.4%) | 14.5 (32.4%) |

$AUC_{tau}$: Area under the concentration-time curve at steady state; $C_{14\,h}$: concentration at 14 h post-dose at steady state; $C_{max}$: maximum concentration at steady state; $C_{min}$: concentration at 24 h post-dose at steady state; CV %: coefficient of variation; Min: minimum; Max: maximum; n: number of subjects.

TABLE 9

Simulations to Support Dosing in Sub-Populations - Adult Patients (Narcolepsy/OSA, tablet, fasting conditions) with Severe Renal Impairment

| Parameters | Reference (Adult, Dose = 150 mg, Normal Renal Function) | Dose | | | |
|---|---|---|---|---|---|
| | | 37.5 mg (n = 10000) | 75 mg (n = 10000) | 150 mg (n = 10000) | 300 mg (n = 10000) |
| $AUC_{tau}$ (ng · h/mL) | | | | | |
| Mean (CV %) | 8874 (34.4%) | 5967 (36.9%) | 12790 (36.8%) | 27416 (36.8%) | 58772 (36.8%) |
| Median | 8382 | 5608 | 12026 | 25790 | 55249 |
| [Min, Max] | [2165, 35375] | [1448, 20711] | [3129, 44391] | [6762, 95179] | [14323, 205161] |
| Geom. Mean (Geom. CV %) | 8387 (34.6%) | 5602 (36.6%) | 12009 (36.6%) | 25744 (36.6%) | 55188 (36.5%) |
| $C_{max}$ (ng/mL) | | | | | |
| Mean (CV %) | 835 (24.8%) | 353 (29.3%) | 738 (29.7%) | 1546 (30.1%) | 3243 (30.5%) |
| Median | 811 | 338 | 705 | 1475 | 3089 |
| [Min, Max] | [323, 2086] | [116, 1014] | [240, 2150] | [496, 4561] | [1029, 9681] |
| Geom. Mean (Geom. CV %) | 810 (24.8%) | 339 (28.8%) | 708 (29.2%) | 1482 (29.6%) | 3105 (30.0%) |
| $C_{min}$ (ng/mL) | | | | | |
| Mean (CV %) | 110 (71.5%) | 163 (49.6%) | 360 (48.6%) | 794 (47.6%) | 1748 (46.8%) |
| Median | 92.2 | 149 | 330 | 728 | 1608 |
| [Min, Max] | [0.362, 961] | [15.8, 737] | [37.9, 1606] | [90.0, 3498] | [212, 7613] |
| Geom. Mean (Geom. CV %) | 84.9 (92.1%) | 145 (52.5%) | 322 (51.0%) | 713 (49.7%) | 1576 (48.6%) |
| $C_{14\,h}$ (ng/mL) | | | | | |
| Mean (CV %) | 268 (46.9%) | 231 (39.7%) | 498 (39.4%) | 1076 (39.0%) | 2322 (38.8%) |
| Median | 248 | 216 | 468 | 1010 | 2178 |
| [Min, Max] | [9.32, 1390] | [45.4, 841] | [101, 1816] | [226, 3919] | [498, 8460] |
| Geom. Mean (Geom. CV %) | 240 (52.2%) | 214 (40.1%) | 464 (39.7%) | 1002 (39.3%) | 2164 (38.9%) |
| Half-life (h) | | | | | |
| Mean (CV %) | 7.30 (30.7%) | 19.7 (33.1%) | 21.1 (33.0%) | 22.6 (33.0%) | 24.2 (33.0%) |
| Median | 6.99 | 18.7 | 20.0 | 21.5 | 23.0 |

TABLE 9-continued

Simulations to Support Dosing in Sub-Populations - Adult Patients (Narcolepsy/OSA, tablet, fasting conditions) with Severe Renal Impairment

| Parameters | Reference (Adult, Dose = 150 mg, Normal Renal Function) | Dose | | | |
|---|---|---|---|---|---|
| | | 37.5 mg (n = 10000) | 75 mg (n = 10000) | 150 mg (n = 10000) | 300 mg (n = 10000) |
| [Min, Max] | [1.96, 24.5] | [5.21, 70.6] | [5.57, 75.7] | [5.96, 81.1] | [6.37, 86.9] |
| Geom. Mean (Geom. CV %) | 6.98 (30.4%) | 18.7 (32.9%) | 20.0 (32.9%) | 21.5 (32.8%) | 23.0 (32.8%) |

$AUC_{tau}$: Area under the concentration-time curve at steady state; $C_{14\,h}$: concentration at 14 h post-dose at steady state; $C_{max}$: maximum concentration at steady state; $C_{min}$: concentration at 24 h post-dose at steady state; CV %: coefficient of variation; Min: minimum; Max: maximum; n: number of subjects.

TABLE 10

Simulations to Support Dosing in Sub-Populations - Adult Patients (Narcolepsy/OSA, tablet, fasting conditions) with ESRD

| Parameters | Reference (Adult, Dose = 150 mg, Normal Renal Function) | Dose | | | |
|---|---|---|---|---|---|
| | | 37.5 mg (n = 10000) | 75 mg (n = 10000) | 150 mg (n = 10000) | 300 mg (n = 10000) |
| $AUC_{tau}$ (ng · h/mL) | | | | | |
| Mean (CV %) | 8874 (34.4%) | 25371 (42.5%) | 54399 (42.6%) | 116645 (42.7%) | 250132 (42.7%) |
| Median | 8382 | 23288 | 49948 | 107070 | 229500 |
| [Min, Max] | [2165, 35375] | [5989, 136885] | [12737, 292530] | [27087, 625152] | [57605, 1335983] |
| Geom. Mean (Geom. CV %) | 8387 (34.6%) | 23394 (41.7%) | 50152 (41.8%) | 107514 (41.8%) | 230486 (41.9%) |
| $C_{max}$ (ng/mL) | | | | | |
| Mean (CV %) | 835 (24.8%) | 1153 (39.8%) | 2456 (40.0%) | 5234 (40.3%) | 11162 (40.5%) |
| Median | 811 | 1065 | 2267 | 4827 | 10282 |
| [Min, Max] | [323, 2086] | [290, 5893] | [617, 12563] | [1310, 26789] | [2786, 57133] |
| Geom. Mean (Geom. CV %) | 810 (24.8%) | 1074 (38.6%) | 2286 (38.9%) | 4868 (39.1%) | 10373 (39.4%) |
| $C_{min}$ (ng/mL) | | | | | |
| Mean (CV %) | 110 (71.5%) | 961 (45.7%) | 2075 (45.6%) | 4476 (45.4%) | 9655 (45.3%) |
| Median | 92.2 | 876 | 1891 | 4084 | 8816 |
| [Min, Max] | [0.362, 961] | [183, 5509] | [398, 11801] | [862, 25275] | [1866, 54124] |
| Geom. Mean (Geom. CV %) | 84.9 (92.1%) | 875 (45.6%) | 1889 (45.3%) | 4079 (45.1%) | 8803 (45.0%) |
| $C_{14\,h}$ (ng/mL) | | | | | |
| Mean (CV %) | 268 (46.9%) | 1045 (43.0%) | 2243 (43.0%) | 4814 (43.0%) | 10333 (43.1%) |
| Median | 248 | 958 | 2056 | 4413 | 9473 |
| [Min, Max] | [9.32, 1390] | [236, 5689] | [505, 12161] | [1079, 25995] | [2304, 55566] |
| Geom. Mean (Geom. CV %) | 240 (52.2%) | 962 (42.3%) | 2064 (42.2%) | 4430 (42.3%) | 9509 (42.3%) |
| Half-life (h) | | | | | |
| Mean (CV %) | 7.30 (30.7%) | 83.6 (38.1%) | 89.7 (38.2%) | 96.1 (38.3%) | 103 (38.4%) |
| Median | 6.99 | 77.9 | 83.4 | 89.6 | 95.9 |
| [Min, Max] | [1.96, 24.5] | [20.8, 337] | [22.3, 363] | [23.9, 392] | [25.5, 422] |
| Geom. Mean (Geom. CV %) | 6.98 (30.4%) | 78.1 (38.1%) | 83.7 (38.2%) | 89.8 (38.2%) | 96.2 (38.3%) |

$AUC_{tau}$: Area under the concentration-time curve at steady state; $C_{14\,h}$: concentration at 14 h post-dose at steady state; $C_{max}$: maximum concentration at steady state; $C_{min}$: concentration at 24 h post-dose at steady state; CV %: coefficient of variation; Min: minimum; Max: maximum; n: number of subjects.

Ratios were generated to facilitate the comparison across populations of patients with renal impairment in order to optimally match the exposure of the reference dose in adult patients with normal renal function (i.e., 150 mg). Ratios of $AUC_{tau}$, $C_{max}$, $C_{min}$, $C_{14h}$ and $t_{1/2}$ are presented in Table 11.

TABLE 11

Ratio of Mean Steady State PK Parameters of Solriamfetol in Patients with Renal Impairment (at different doses) Relative to Patients with Normal Renal Function (at 150 mg dose)

| Sub-Population | Dose (mg) | Ratio Relative to Typical Patient with Normal Renal Function | | | | |
|---|---|---|---|---|---|---|
| | | $AUC_{tau}$ | $C_{max}$ | $C_{14h}$ | $C_{min}$ | $t_{1/2}$ |
| Mild Renal Impairment | 300 | 2.91 | 2.33 | 3.37 | 4.38 | 1.47 |
| | 150 | 1.36 | 1.13 | 1.53 | 1.92 | 1.36 |
| | 75 | 0.63 | 0.55 | 0.70 | 0.83 | 1.27 |
| | 37.5 | 0.30 | 0.27 | 0.32 | 0.36 | 1.19 |
| Moderate Renal Impairment | 300 | 4.16 | 2.83 | 5.17 | 8.07 | 2.08 |
| | 150 | 1.94 | 1.36 | 2.38 | 3.61 | 1.95 |
| | 75 | 0.90 | 0.66 | 1.09 | 1.61 | 1.81 |
| | 37.5 | 0.42 | 0.32 | 0.50 | 0.71 | 1.70 |
| Severe Renal Impairment | 300 | 6.62 | 3.88 | 8.66 | 15.89 | 3.32 |
| | 150 | 3.09 | 1.85 | 4.01 | 7.22 | 3.10 |
| | 75 | 1.44 | 0.88 | 1.86 | 3.27 | 2.89 |
| | 37.5 | 0.67 | 0.42 | 0.89 | 1.48 | 2.70 |
| ESRD | 300 | 28.19 | 13.37 | 36.56 | 87.77 | 14.11 |
| | 150 | 13.1 | 6.27 | 18.0 | 40.7 | 13.2 |
| | 75 | 6.13 | 2.94 | 8.37 | 18.9 | 12.3 |
| | 37.5 | 2.86 | 1.38 | 3.90 | 8.74 | 11.5 |

$AUC_{tau}$: Area under the concentration-time curve at steady state; $C_{max}$: maximum concentration at steady state; $C_{14h}$: concentration at 14 h post-dose at steady state; $C_{min}$: concentration at 24 h post-dose at steady state; $t_{1/2}$: elimination half-life.

Based on the inventor's analyses of solriamfetol's pharmacokinetics and safety profile together with population PK simulations, it was discovered that, in patients with mild renal impairment, an equivalent dose used in patients with normal renal function was associated with comparable exposures. A 150 mg dose in patients with mild renal impairment is associated with $AUG_{tau}$ and $C_{max}$ values 36% and 13% higher than those observed in patients with normal renal function for the same dose. Typical $C_{14h}$ and $C_{min}$ values in a patient with mild renal impairment are expected to be approximately 1.5- and 2-fold higher than that observed in patients with normal renal function due to the longer $t_{1/2}$. Therefore, no dosage adjustments should be needed in patients with mild renal impairment and this subgroup of renally impaired patients can be safety administered at an initial daily dose equivalent to 75 mg of solriamfetol and escalating to a maximum daily dose equivalent to 150 mg of solriamfetol after at least 3 days, based on solriamfetol's elimination half-life.

In patients with moderate renal impairment, one-half of the dose used in patients with normal renal function was associated with comparable exposures. A 75 mg dose in patients with moderate renal impairment is associated with $AUC_{tau}$ and $C_{max}$ values 10% and 34% lower than those observed in patients with normal renal function at a 150 mg dose. Typical $C_{14h}$ and $C_{min}$ values in a patient with moderate renal impairment is expected to be approximately 9% and 61% higher than that observed in patients with normal renal function due to the longer $t_{1/2}$. Therefore, dosing adjustments are warranted in patients with moderate renal impairment. The appropriate dose escalation regimen for this subgroup of renally impaired patients was determined by the present inventor to be an initial daily dose equivalent to 37.5 mg solriamfetol and escalating to a maximum daily dose equivalent to 75 mg solriamfetol after at least five days to at least seven days, based on solriamfetol's elimination half-life.

In patients with severe renal impairment, one-quarter of the dose used in patients with normal renal function was associated with comparable exposures. A 75 mg dose in patients with severe renal impairment was associated with $AUC_{tau}$ and $C_{max}$ values 44% higher and 12% lower than those in patients with normal renal function at a 150 mg dose. Typical $C_{14h}$ and $C_{min}$ following a 75 mg dose in patients with severe renal impairment is expected to be approximately 1.9- and 3-fold higher than that in patients with normal renal function. Therefore, it was determined that a 75 mg dose would not be appropriate for patients with severe renal impairment. Therefore, dosing adjustment is warranted in patients with severe renal impairment. A 37.5 mg dose in patients with severe renal impairment was associated with $AUC_{tau}$ and $C_{max}$ values 33% lower and 58% lower than those in patients with normal renal function at a 150 mg dose. Typical $C_{14h}$ and $C_{min}$ values following a 37.5 mg dose in a patient with severe renal impairment are expected to be 14% lower and 48% higher than that in patients with normal renal function. Therefore, dosing adjustments is warranted in patients with severe renal impairment. The appropriate dose escalation regimen for this subgroup of renally impaired patients was determined by the present inventor to be a daily maximum dose equivalent to 37.5 mg of solriamfetol.

Based on the substantial increase in solriamfetol exposure in patients with ESRD, use of solriamfetol in this subpopulation should be avoided.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

What is claimed is:

1. A method of treating excessive daytime sleepiness in a subject in need thereof having moderate or severe renal impairment, said method comprising:
   selecting a subject that has not been treated with a monoamine oxidase inhibitor within the preceding 14 days;
   determining the estimated glomerular filtration rate (eGFR) of the subject, and
   (a) providing to the subject having an eGFR of about 30 mL/min/1.73 m² to about 59 mL/min/1.73 m²:
      a first oral daily dose equivalent to 37.5 mg [R]-2-amino-3-phenylpropylcarbamate (APC) from day one to day $n_1$ of a dose escalation regimen, and
      a second oral daily dose equivalent to 75 mg APC starting on day $n_2$ of the dose escalation regimen,
   wherein $n_1$ is an integer equal to or greater than 5 and $n_2$ is equal to the sum of $n_1+1$,
   wherein the subject is not provided a daily dose exceeding a dose equivalent to 75 mg APC; and
   (b) providing to the subject having an eGFR of about 15 mL/min/1.73 m² to about 29 mL/min/1.73 m²:
      an oral daily dose equivalent to 37.5 mg APC,
   wherein the subject is not provided a daily dose exceeding a dose equivalent to 37.5 mg APC.

2. The method of claim 1, wherein the excessive daytime sleepiness is due to narcolepsy.

3. The method of claim 1, wherein the excessive daytime sleepiness is due to obstructive sleep apnea.

4. The method of claim 1, wherein the excessive daytime sleepiness is due to shift work disorder.

5. The method of claim 1, wherein the subject is provided said first oral daily dose or said oral daily dose in the form of about 44.7 mg APC-HCl.

6. The method of claim 1, wherein the subject is provided said second oral daily dose in the form of about 89.3 mg APC-HCl.

7. The method of claim 1, wherein said first oral daily dose, said second oral daily dose, and said oral daily dose are each administered upon the subject's awakening.

8. The method of claim 1, wherein said first oral daily dose, said second oral daily dose, and said oral daily dose are each administered more than nine hours in advance of the subject's bedtime.

9. The method of claim 1, wherein the subject is a human.

10. The method of claim 1, wherein the eGFR is determined using the Modification in Diet in Renal Disease equation.

11. The method of claim 1, wherein $n_1$ is an integer equal to or greater than 7.

12. A method of treating excessive daytime sleepiness in a subject in need thereof having no, mild, moderate, or severe renal impairment, said method comprising:
   selecting a subject that has not been treated with a monoamine oxidase inhibitor within the preceding 14 days;
   determining the estimated glomerular filtration rate (eGFR) of the subject, and
   (a) providing to the subject having an eGFR of about 30 mL/min/1.73 m$^2$ to about 59 mL/min/1.73 m$^2$:
   a first oral daily dose equivalent to 37.5 mg [R]-2-amino-3-phenylpropylcarbamate (APC) from day one to day $n_1$ of a dose escalation regimen, and
   a second oral daily dose equivalent to 75 mg APC starting on day $n_2$ of the dose escalation regimen,
   wherein $n_1$ is an integer equal to or greater than 5 and $n_2$ is equal to the sum of $n_1+1$,
   wherein the subject is not provided a daily dose exceeding a dose equivalent to 75 mg APC;
   (b) providing to the subject having an eGFR of about 15 mL/min/1.73 m$^2$ to about 29 mL/min/1.73 m$^2$:
   an oral daily dose equivalent to 37.5 mg APC,
   wherein the subject is not provided a daily dose exceeding a dose equivalent to 37.5 mg APC; and
   (c) providing to the subject having an eGFR of about 60 mL/min/1.73 m$^2$ to about 89 mL/min/1.73 m$^2$ or about 90 mL/min/1.73 m$^2$ or greater:
   a first oral daily dose equivalent to 37.5 mg APC,
   after at least 3 days a second oral daily dose equivalent to 75 mg APC, and
   after at least 3 days a third oral daily dose equivalent to 150 mg APC,
   wherein the subject is not provided a daily dose exceeding a dose equivalent to 150 mg APC.

13. The method of claim 12, wherein the excessive daytime sleepiness is due to narcolepsy.

14. The method of claim 12, wherein the excessive daytime sleepiness is due to obstructive sleep apnea.

15. The method of claim 12, wherein the excessive daytime sleepiness is due to shift work disorder.

16. The method of claim 12, wherein the subject is provided said first oral daily dose or said oral daily dose in the form of about 44.7 mg APC-HCl.

17. The method of claim 12, wherein the subject is provided said second oral daily dose in the form of about 89.3 mg APC-HCl.

18. The method of claim 12, wherein the subject is provided said third oral daily dose in the form of about 178.5 mg APC-HCl.

19. The method of claim 12, wherein said first oral daily dose, said second oral daily dose, said third daily dose, and said oral daily dose are each administered upon the subject's awakening.

20. The method of claim 12, wherein said first oral daily dose, said second oral daily dose, said third daily dose, and said oral daily dose are each administered more than nine hours in advance of the subject's bedtime.

21. The method of claim 12, wherein the subject is a human.

22. The method of claim 12, wherein the eGFR is determined using the Modification in Diet in Renal Disease equation.

23. The method of claim 12, wherein $n_1$ is an integer equal to or greater than 7.

24. The method of claim 1, wherein the excessive daytime sleepiness is due to depression.

25. The method of claim 12, wherein the excessive daytime sleepiness is due to depression.

* * * * *

UNITED STATES PATENT AND TRADEMARK OFFICE
CERTIFICATE OF CORRECTION

PATENT NO. : 11,850,227 B2  
APPLICATION NO. : 18/194503  
DATED : December 26, 2023  
INVENTOR(S) : Katayoun Zomorodi Page 1 of 1

It is certified that error appears in the above-identified patent and that said Letters Patent is hereby corrected as shown below:

In the Claims

Claim 10, Line 2: "Modification in Diet" should read -- Modification of Diet --.

Claim 22, Line 2: "Modification in Diet" should read -- Modification of Diet --.

Signed and Sealed this  
Ninth Day of April, 2024

Katherine Kelly Vidal  
*Director of the United States Patent and Trademark Office*